(12) United States Patent
Baunoch et al.

(10) Patent No.: US 10,160,991 B2
(45) Date of Patent: Dec. 25, 2018

(54) ASSAY FOR THE COMPREHENSIVE IDENTIFICATION OF ANTIBIOTIC SENSITIVITY

(71) Applicant: CAP Diagnostics, LLC, Irvine, CA (US)

(72) Inventors: David A. Baunoch, Irvine, CA (US); Miguel F. R. Penaranda, Irvine, CA (US); Michael L. Opel, Irvine, CA (US); Maher Badir, Irvine, CA (US)

(73) Assignee: CAP DIAGNOSTICS, LLC, Irvine, CA (US)

( * ) Notice: Subject to any disclaimer, the term of this patent is extended or adjusted under 35 U.S.C. 154(b) by 0 days.

(21) Appl. No.: 15/957,780

(22) Filed: Apr. 19, 2018

(65) Prior Publication Data
US 2018/0305730 A1    Oct. 25, 2018

Related U.S. Application Data

(60) Provisional application No. 62/487,395, filed on Apr. 19, 2017.

(51) Int. Cl.
*C12Q 1/02* (2006.01)
*C12Q 1/08* (2006.01)
*G01N 21/59* (2006.01)

(52) U.S. Cl.
CPC ............. *C12Q 1/08* (2013.01); *G01N 21/59* (2013.01)

(58) Field of Classification Search
CPC .................................................. C12Q 1/025
See application file for complete search history.

(56) References Cited

U.S. PATENT DOCUMENTS

| 4,132,599 A | 1/1979 | Picciolo et al. |
| 9,834,808 B2 | 12/2017 | Stern et al. |
| 2004/0005653 A1 | 1/2004 | Chen et al. |
| 2005/0095665 A1 | 5/2005 | Williams et al. |
| 2013/0029981 A1* | 1/2013 | De Keersmaecker ...... C07D 233/88  514/233.2 |
| 2016/0289729 A1 | 10/2016 | Richards et al. |

FOREIGN PATENT DOCUMENTS

| WO | 2015189390 A1 | 12/2015 |
| WO | 2016207065 A1 | 12/2016 |

OTHER PUBLICATIONS

Tally, "Factors affecting the choice of antibiotics in mixed infections," J Antimicrobial Chemotherapy 22(Suppl. A):87-100, 1988.*
El-Azizi, "Novel microdilution method to assess double and triple antibiotic combination therapy in vitro," Int J Microbiol, Hindawi Publishing Corp., article No. 4612021, Mar. 29, 2016.*

(Continued)

*Primary Examiner* — Rosanne Kosson
(74) *Attorney, Agent, or Firm* — K&L Gates LLP; Louis C. Cullman; Michelle Glasky Bergman

(57) ABSTRACT

Disclosed herein are methods determining susceptibility of bacteria in a sample from a subject suspected of having an infection to a plurality of antibiotics simultaneously, wherein the sample is tested without first isolating the bacteria from the sample.

25 Claims, 1 Drawing Sheet

|   | 1 | 2 | 3 | 4 | 5 | 6 |
|---|---|---|---|---|---|---|
| A | No antibiotic | Mero (20) | Levo (40) | Ceftriaxone (640) | Pip/Tazo (640,40) | Tetra (160) |
| B | Nitro (320) | Mero (40) | Levo (80) | Vanco (20) | Pip/Tazo (1280,40) | Amp (80) |
| C | Nitro (640) | Mero (80) | Ceftriaxone (10) | Vanco (40) | Cefoxitin (40) | Amp (160) |
| D | Nitro (1280) | Amp/Sulb (80,40) | Ceftriaxone (20) | Vanco (80) | Cefoxitin (80) | Amp (320) |
| E | Cipro (10) | Amp/Sulb (160,80) | Ceftriaxone (40) | Vanco (160) | Cefoxitin (160) | TMP/SMX (20,380) |
| F | Cipro (20) | Amp/Sulb (320,160) | Ceftriaxone (80) | Vanco (320) | Cefoxitin (320) | TMP/SMX (40,760) |
| G | Cipro (40) | Levo (10) | Ceftriaxone (160) | Pip/Tazo (160,40) | Tetra (40) | AB-blend |
| h | Mero (10) | Levo (20) | Ceftriaxone (320) | Pip/Tazo (320,40) | Tetra (80) | empty |

(56) References Cited

OTHER PUBLICATIONS

Mohan et al., A microfluidic approach to study the effect of bacterial interactions on antimicrobial susceptibility in polymicrobial cultures. RSC Advances, vol. 5, pp. 35211-35223 (2015).

Sun et al., Rapid antimicrobial susceptibility test for identification of new therapeutics and drug combinations against multidrug-resistant bacteria. Emerging Microbes & Infections, vol. 5 (2016).

International Search Report and Written Opinion dated Jul. 16, 2018 for International Application No. PCT/US2018/028422 filed on Apr. 19, 2018.

Alteri et al., Preferential use of central metabolism in vivo reveals a nutritional basis for polymicrobial infection. PLoS Pathog, 11(1): e1004601 (2015).

Croxall et al., Increased human pathogenic potential of *Escherichia coli* from polymicrobial urinary tract infections in comparison to isolates from monomicrobial culture samples. J Med Microbiol., 60(Pt 1):102-9 (2011).

Hollick et al., Comparison of direct and standarized disk diffusion susceptibility testing of urine cultures. Antimicrobial Agents and Chemotherapy, vol. 9, No. 5, pp. 804-809 (1976).

Johnson et al., Direct antimicrobial susceptibility testing for acute urinary tract infections in women. Journal of clinical Microbiology, vol. 33, No. 9, pp. 2316-2323 (1995).

Kline et al., Gram-positive uropathogens, polymicrobial urinary tract infection, and the emerging microbiota of the urinary tract. Microbiol Spectr., 4(2), 54 pp. (2016).

Cockerill et al., Methods for dilution antimicrobial susceptibility tests for bacteria that grow aerobically; approved standard—Ninth edition. Clinical and Laboratory Standards Institute, M07-A9, vol. 32, No. 2 replaces M07-A8, vol. 29, No. 2 (2012).

Wolfe et al., Evidence of uncultivated bacteria in the adult female bladder. Journal of Clinicial Microbiology, vol. 50, No. 4, pp. 1376-1383 (2012).

Shahidi A. and Ellner P.D. "Effect of Mixed Cultures on Antibiotic Susceptibility Testing," Applied Microbiology 18:766-770, 1969.

Guidance for Industry and FDA. Class II Special Controls Guidance Document: Antimicrobial Susceptibility Test (AST) Systems. US Department of Health and Human Services, Food and Drug Administration, Center for Devices and Radiological Health, Bacteriology Branch, Division of Microbiology Devices, Office of in Vitro Diagnostic Device (OIVD) Evaluation and Safety. Aug. 28, 2009.

Procedures/Guidelines for the Microbiology Laboratory, College of Physicians & Surgeons of Saskatchewan Laboratory Quality Assurance Program. 2016.

Gundersen Health System Standard Operating Procedure. Vitek 2 Compact—Identification and Susceptibility Testing. https://www.gundersenhealth.org/app/files/public/6557/Lab-Policies-Vitek-2-Compact-Identification-and-Susceptibility-Testing-Lab-1512.pdf. Jan. 5, 2018.

College of American Pathologies, Microbiology Checklist, Aug. 21, 2017.

Dijkshoorn L et al. "Strain, clone and species: comments on the three basic concepts of bacteriology," J. Med. Microbiol. 49:397-401, 2000.

Mohan R et al. "A microfluidic approach to study the effect of bacterial interactions on antimicrobial susceptibility in polymicrobial cultures," RSC Advances 5:35211-35223, 2015.

Sun W et al. "Rapid antimicrobial susceptibility test for identification of new therapeutics and drug combinations against multidrug-resistant bacteria," Emerging Microbes and Infections 5:e116, 2016.

\* cited by examiner

FIG. 1

|   | 1 | 2 | 3 | 4 | 5 | 6 |
|---|---|---|---|---|---|---|
| A | No antibiotic | Mero (20) | Levo (40) | Ceftriaxone (640) | Pip/Tazo (640,40) | Tetra (160) |
| B | Nitro (320) | Mero (40) | Levo (80) | Vanco (20) | Pip/Tazo (1280,40) | Amp (80) |
| C | Nitro (640) | Mero (80) | Ceftriaxone (10) | Vanco (40) | Cefoxitin (40) | Amp (160) |
| D | Nitro (1280) | Amp/Sulb (80,40) | Ceftriaxone (20) | Vanco (80) | Cefoxitin (80) | Amp (320) |
| E | Cipro (10) | Amp/Sulb (160,80) | Ceftriaxone (40) | Vanco (160) | Cefoxitin (160) | TMP/SMX (20,380) |
| F | Cipro (20) | Amp/Sulb (320,160) | Ceftriaxone (80) | Vanco (320) | Cefoxitin (320) | TMP/SMX (40,760) |
| G | Cipro (40) | Levo (10) | Ceftriaxone (160) | Pip/Tazo (160,40) | Tetra (40) | AB-blend |
| h | Mero (10) | Levo (20) | Ceftriaxone (320) | Pip/Tazo (320,40) | Tetra (80) | empty |

FIG. 2

|   | 1 | 2 | 3 | 4 | 5 | 6 | 7 | 8 |
|---|---|---|---|---|---|---|---|---|
| A | No-Antibiotic | Mero (80) | Ceftriaxone (40) | Pip/Tazo (160,40) | Tetra (160) | Cefazolin (160) | Ceftazidime (40) | No-Antibiotic |
| B | Nitro (320) | Amp/Sulb (80,40) | Ceftriaxone (80) | Pip/Tazo (1280,40) | Amp (80) | Cefazolin (320) | Ceftazidime (80) | No-Antibiotic |
| C | Nitro (1280) | Amp/Sulb (320,160) | Ceftriaxone (640) | Cefoxitin (40) | Amp (160) | Cefepime (10) | Ceftazidime (160) | Cefaclor (80) |
| D | Cipro (10) | Levo (10) | Vanco (10) | Cefoxitin (80) | Amp (320) | Cefepime (20) | Ceftazidime (320) | Cefaclor (320) |
| E | Cipro (40) | Levo (20) | Vanco (20) | Cefoxitin (320) | TMP/SMX (20,380) | Cefepime (40) | Gentamicin (40) | Na Azide |
| F | Mero (10) | Levo (40) | Vanco (40) | Tetra (20) | TMP/SMX (40,760) | Cefepime (80) | Gentamicin (160) | No-Antibiotic |
| G | Mero (20) | Levo (80) | Vanco (160) | Tetra (40) | Cefazolin (20) | Cefepime (160) | Amox/Clav (80,40) | No-Antibiotic |
| H | Mero (40) | Ceftriaxone (10) | Vanco (320) | Tetra (80) | Cefazolin (80) | Cefepime (320) | Amox/Clav (320,160) | No-Antibiotic |

ASSAY FOR THE COMPREHENSIVE IDENTIFICATION OF ANTIBIOTIC SENSITIVITY

CROSS-REFERENCE TO RELATED APPLICATIONS

The present application claims the benefit of U.S. Provisional application 62/487,395 filed Apr. 19, 2017, the entire contents of which are incorporated by reference herein.

FIELD

The present application is regarding antibiotic suspectibility assays.

BACKGROUND

Infectious disease affect multiple organs systems and are responsible for significant morbidity, mortality, and economic impact. Infectious agents most often present as a complex polymicrobial infections rather than as a single pathogens. Within the body, these polymicrobial infections cooperate with each other through mutualism changing both the type of antibiotics the organisms are susceptible to but also the level of antibiotics required to treat the infection as well as the virulence of the individual pathogens. The current gold standard is culture and sensitivity; a process in which a sample of is placed on a plate containing an agar medium for an overnight incubation allowing for individual organisms to be isolated and identified. An additional day is usually required to identify which antibiotic the individual organism is susceptible to through antibiotic susceptibility testing. The effectiveness of the this process is limited by the inherently poor sensitivity and specificity of the methodology. For example, recent studies have found that up to 25% of all urine culture results produce a false negative finding and that up to ⅔ of all uropathogens are missed by culture. This process which typically takes 48-72 hours has a significant impact on clinical practice in that clinicians are forced to treat the patient empirically without an accurate diagnosis and without proper guidance regarding the type of antibiotic that would be effective for treating the infection.

An inherent flaw in current antibiotic susceptibility testing is that it relies on testing only an individual organism rather than the entire pool of organisms simultaneously. By necessitating the isolation it adds a minimum of one additional day to the testing process. There is a need for a test that allows for the simultaneous assessment of antibiotic resistance without the need for isolation allowing for a more rapid determination of antibiotic resistance. The method described herein is a simple cost effective methods for assessing antibiotic resistance in all constituents simultaneously without the need for prior isolation.

SUMMARY

Disclosed herein are methods for determining the antibiotic sensitivity of a mixed population of bacteria present in patient samples to multiple antibiotics simultaneously without first isolating the bacteria from the sample.

In some embodiments, disclosed herein are methods for determining susceptibility of a mixed population of bacteria in a sample to a plurality of antibiotics simultaneously, the method comprising: applying a quantity of the sample simultaneously to a plurality of antibiotic-containing medium, wherein the sample is from a subject suspected of having an infection; culturing the sample on the medium for a period of time; suspending bacteria present in the medium with a solution and recovering the suspension; measuring an $OD_{600}$ of the suspension, wherein an adjusted $OD_{600}$ of a suspension indicates the susceptibility or resistance of bacteria in the sample to an individual antibiotic; and providing the susceptibility information to a medical professional to determine antibiotic therapy for the subject. The sample is suspected of having multiple species of bacteria therein.

In some embodiments, the plurality of antibiotic-containing medium comprises a multi-well assay plate having disposed in a plurality of wells antibiotic-containing bacterial growth medium. In some embodiments, the multi-well assay plate has 96 wells. In some embodiments, the bacterial growth medium is an agar-containing medium.

In some embodiment, the plurality of antibiotics comprises two or more of sulfamethoxazole, trimethoprim, nitrofurantoin, fosfomycin, amoxicillin, clavulanate, cefpodoxime, cefdinir, cefaclor, cefepime, cefazolin, ciprofloxacin, levofloxacin, ceftriaxone, gentamicin, tobramycin, avibactam, ceftazidime, ceftolozane, tazobactam, norfloxacin, meropenem, piperacillin, cefoxitin, tetracycline, sulbactam, cefuroxime, and vancomycin. In some embodiments, each of the plurality of wells contains a single antibiotic or a combination of antibiotics. In some embodiment, the combination of antibiotics comprises two antibiotics. In some embodiment, the plurality of antibiotics comprises at least three antibiotics, at least four antibiotics, at least five antibiotics, at least six antibiotics, at least seven antibiotics, at least eight antibiotics, at least nine antibiotics, or at least ten antibiotics. In some embodiments, each antibiotic, or combination of antibiotics, is present in the wells at two or more concentrations. In some embodiment, each antibiotic, or combination of antibiotics, is present in the wells at three or more concentrations.

In some embodiments, the $OD_{600}$ of the suspension is measured a plurality of times. In some embodiments, the $OD_{600}$ is measured twice, three times, four times, or five times. In some embodiments, the adjusted $OD_{600}$ comprises the mean $OD_{600}$ of a plurality of measurements less a background control. In some embodiments, the bacteria in the sample are susceptible to an antibiotic, or combination of antibiotics, if the adjusted $OD_{600}$ is less than 0.025. In some embodiments, the bacteria in the sample are resistant to an antibiotic, or combination of antibiotics, if the adjusted $OD_{600}$ is greater than or equal to 0.025.

In some embodiments, the sample is a biological fluid or a biopsy sample. In some embodiments, the sample comprises urine, blood, saliva, sputum, pulmonary lavage, vaginal secretions, biopsy tissue, or cerebrospinal fluid.

Also disclosed herein are methods for determining susceptibility of a mixed population of bacteria in a sample to a plurality of antibiotics simultaneously, the method comprising: mixing a quantity of a sample with growth medium and incubating for a period of time; applying the sample simultaneously to a plurality of antibiotic-containing medium, wherein the sample is from a subject suspected of having an infection; culturing the sample in the antibiotic-containing medium for a period of time; measuring bacterial growth in the medium by $OD_{600}$ measurement, wherein an adjusted $OD_{600}$ measurement of the sample indicates the susceptibility or resistance of the bacteria in the sample to an individual antibiotic; and providing the susceptibility information to a medical professional to determine antibiotic therapy for the subject. The sample is suspected of having multiple species of bacteria therein.

In some embodiments, the plurality of antibiotic-containing medium comprises a multi-well assay plate having disposed in a plurality of wells antibiotic-containing bacterial growth medium. In some embodiments, the multi-well assay plate has 96-wells. In some embodiments, the medium is a liquid broth medium. In some embodiments, the medium is Mueller-Hinton medium.

In some embodiments, the plurality of antibiotics comprises two or more of sulfamethoxazole, trimethoprim, nitrofurantoin, fosfomycin, amoxicillin, clavulanate, cefpodoxime, cefdinir, cefaclor, ciprofloxacin, levofloxacin, ceftriaxone, gentamicin, tobramycin, avibactam, ceftazidime, ceftolozane, tazobactam, norfloxacin, meropenem, piperacillin, cefoxitin, tetracycline, sulbactam, cefuroxime, and vancomycin. In some embodiments, each of the plurality of wells contains a single antibiotic or a combination of antibiotics. In some embodiments, the combination of antibiotics comprises two antibiotics. In some embodiments, the plurality of antibiotics comprises at least three antibiotics, at least four antibiotics, at least five antibiotics, at least six antibiotics, at least seven antibiotics, at least eight antibiotics, at least nine antibiotics, or at least ten antibiotics. In some embodiments, each antibiotic, or combination of antibiotics, is present in the wells at two or more concentrations. In some embodiments, each antibiotic, or combination of antibiotics, is included at three or more concentrations.

In some embodiments, the $OD_{600}$ of the sample is measured one time. In some embodiments, the $OD_{600}$ of the sample is measured a plurality of times. In some embodiments, the $OD_{600}$ is measured twice, three times, four times, or five times. In some embodiments, the adjusted $OD_{600}$ comprises a single $OD_{600}$ measurement, or a mean $OD_{600}$ of a plurality of measurements, less a background control. In some embodiments, the bacteria in the sample are susceptible to an antibiotic, or combination of antibiotics, if the adjusted $OD_{600}$ is less than 0.065. In some embodiments, the bacteria in the sample are resistant to an antibiotic, or combination of antibiotics, if the adjusted $OD_{600}$ is greater than or equal to 0.065.

In some embodiments, the sample is a biological fluid or a biopsy sample. In some embodiments, the sample comprises urine, blood, saliva, sputum, pulmonary lavage, vaginal secretions, biopsy tissue, or cerebrospinal fluid.

BRIEF DESCRIPTION OF THE DRAWINGS

FIG. 1 depicts an exemplary Antibiotic Source Plate with well contents and antibiotic concentration (μg/mL). Nitro=nitrofurantoin, Cipro=ciprofloxacin, Mero=meropenem, Ceftiaxone=ceftriaxone, TMP/SMX=trimethoprim+sulfamethoxazole, Pip/Tazo=piperacillin+tazobactam, Levo=levofloxacin, Cefoxitin=cefoxitin, Tetra=tetracycline, Amp/Sulb=ampicillin+sulbactam, Amp=ampicillin, and Vanco=vancomycin.

FIG. 2 depicts an exemplary Antibiotic Source Plate with well contents and antibiotic concentration (μg/mL). Cefazolin=cefazolin, Cefepime=cefepime, Ceftazidime=ceftazidime, Gentamicin=gentamicin, Amox/Clav=amoxicillin+clavulanate, Cefaclor=cefaclor.

DETAILED DESCRIPTION

The diagnosis and management of polymicrobial infections has never been more important especially with an aging population in which polymicrobial infections affecting multiple sites and organ systems have significant impacts both clinically and economically. The diagnosis and management of these infectious diseases is significantly impacted by the poor diagnostic tools available coupled with decreasing efficacy of antibiotics available to combat them. A good model system to evaluate these challenges is the diagnosis and management of urinary tract infections (UTI's).

In the past, urine had been considered a "sterile" liquid and normally would not have bacteria present. Cultures with no bacterial outgrowth were assumed to be bacterial free and it is now know that this may be due to the lack of bacterial growth in the urine culture, not necessarily due to the absence of bacteria. The human bladder is now recognized as having a microbiome including a spectrum of bacterial flora normally present which has been overlooked because of our limited capacity to culture microorganisms. The result of this problem is an understatement of the frequency and scope of bacterial infections.

A recent study (Wolfe et al. J Clin Microbiol 50:1376-1383, 2012) compared urine samples obtained from voided, transurethral, and/or suprapubic collection methods and determined standard culture methodology with PCR amplification of 16S rRNA. This study demonstrated that bacteria were present in at least a subpopulation of the culture-negative transurethral collected urine, the sample least likely to be contaminated with bacteria from other sources (vaginal or rectal contamination). It is estimated that the urine of only about half UTI symptomatic patients results in positive cultures.

Furthermore, it was thought that UTIs were usually due to a single bacteria strain and if, after culture, multiple strains of bacteria were present in a urine specimen, the specimen was presumed to be contaminated during collection. These cultures with multiple strains of bacteria were often discarded and not processed further. It is now recognized that many UTI are polymicrobial and the bacterial strains may cooperate or support each other in colonizing the bladder.

Currently existing urine culture conditions, from the composition of the culture medium, to the pH, gas ratios, and incubation time, are biased for the detection of a subset of pathogens, primarily *Escherichia coli*. However, these biased assays are not consistent with clinical symptoms. Thus, routine testing of urine samples misses many uropathogens.

Due to increase in prevalence of antibiotic-resistant bacteria, treatment of UTIs is often insufficient due to the presence of undiagnosed resistant organisms. Additionally, polymicrobial infections have increased the frequency of antibiotic resistance and virulence compared to monomicrobial infections.

For example, infection with both *Staphylococcus saprophyticus* and *Proteus mirabilis* leads to an increased risk of ascending pyelonephritis; infection with both uropathogenic *E. coli* (UPEC) and *P. mirabilis* results in increased colony forming units (CFU) count for both microbes; infection with both *P. mirabilis* and a *Providencia* strain leads to an increased risk of urinary stones; infection with both *Pseudomonas aeruginosa* and *Enterococcus faecalis* leads to an increased risk of pyelonephritis; and infection with both a Group B *Streptococcus* and UPEC results in an increased titer of UPEC.

The challenges involved in identifying microorganisms and managing the associated polymicrobial infections is not limited to urine. It is in point of fact the norm, rather than the exception, and include infections of the ears, nose and throat, the gastrointestinal tract, kidney stones, nails and skin, the prostate, the respiratory system, presurgical and surgical infections, and wound care. These polymicrobial infections are often complex with large numbers of organisms involved. For example, bacterial prostatitis is caused by between one to eight various pathogens at one time as the pathogens could be discovered in any specific semen sample, and the complete concentration of microorganisms varies from 2.0 to 7.5 log 10 CFU/ml. In cystic fibrosis, the infections are recognized to be genetically and phenotypically diversified, even inside the same patient and separate area of the lung. Infection diversity likely impacts management, and the presence of two or more species inhabiting the same space appears to change the way individual bacterial species behave. Their communications, including distributing genetic data, influence antibiotic susceptibility. The presence of a particular bacteria may be associated with better or worse outcomes.

In surgical site infections, a subcomponent of healthcare-associated infections (HAI) that constitutes 20% of all HAI with surgical site infections developing in roughly 5% of all surgical procedures. Surgical site infections have been shown to arise from polymicrobial infections.

One of the most common sites of polymicrobial infections is in wound care. Pressure sores are most common in aging seniors with impaired mobility and are fairly very difficult to cure. Approximately 26% of the elderly have pressure ulcers at the moment of a hospital stay and the occurrence escalates significantly as a result of age. The ulcer that develops may be associated with some infectious complications. Chronic and acute wounds embody a widespread health issue. Dermal wounds are colonized by both anaerobic and aerobic bacterial and fungal strains, most them belonging to the resident microbiota of the surrounding skin, mouth, and gut, or from the external environment, which form polymicrobial communities.

Kidney stones have shown to involve polymicrobial bacterial agents. The kidney stone is a solid piece of stone or crystals that develops in the urinary tract. Stones may lead to hematuria in the urine, vomiting, or painful urination. Individuals who suffer from chronic UTIs, such as those with long-term tubes in their kidneys or bladders, or people with weak bladder emptying due to neurologic disorders (paralysis, multiple sclerosis, and spina bifida) are the most risk.

Thus, the prevalence of polymicrobial infections requires the development of new methodologies. Using current culture guidelines, polymicrobial infections would most often be classed as mixed flora—probable contamination—and would not be worked up. There are a number of studies showing polymicrobial infections in the blood with corresponding UTI findings supporting the importance of proper characterization of samples. This lack of sensitivity seen with traditional culture coupled with current culture guidelines underlies the growing incidence of patients presenting with symptoms of infection and no diagnosis—resulting in ineffective treatment.

In some embodiments, described herein are antibiotic susceptibility assays for combined microflora (polymicrobial) present in a patient sample. Thus, the samples assayed in the present method comprise the sample which is optionally stored, and optionally diluted, prior to testing. No bacteria are isolated from the sample prior to antibiotic sensitivity testing. The disclosed method identifies the antibiotics necessary to treat organisms found within the sample in a biological context and determines the minimal inhibitory concentration (MIC) for the desired antibiotics.

As used herein, the term "sample" refers to any biological fluid or tissue collected from a subject suspected of having an infection. Exemplary "samples" include, but are not limited to, urine, blood, saliva, sputum, pulmonary lavage, fecal material, vaginal secretions, biopsy tissue, cerebrospinal fluid, or any bodily fluid or tissue in need of antibiotic susceptibility assay.

As used herein, the term "subject" refers to any mammalian subject for which antibiotic susceptibility testing is desired and includes, but is not limited to, humans, companion animals (e.g., dogs, cats, guinea pigs, hamsters, ferrets, rabbits, rats, mice, etc.), livestock (e.g., cattle, swine, sheep, goats, horses, etc.), and any other mammal suspected of having an infection and in need of antibiotic susceptibility assay.

As used herein, the term "bacteria" can refer to a single species or multiple species.

As used herein, the term "polymicrobial" refers to a sample having present therein multiple species of bacteria. Polymicrobial samples are also referred to as having a mixed population of bacteria.

As used herein, the term "susceptible" refers to bacteria which are inhibited by the usually achievable concentrations of antimicrobial agent when the dosage recommended to treat the site of infection is used.

As used herein, the term "resistant" refers to bacteria which are not inhibited by the usually achievable concentrations of the antibiotic with normal dosage schedules and/or that demonstrate minimal inhibitory concentrations that fall in the range in which specific microbial resistance mechanisms (e.g., β-lactamases) are likely, and clinical efficacy of the agent against the isolate has not been reliably shown in treatment studies.

The minimal inhibitory concentration (MIC) is the lowest concentration of an antimicrobial agent that prevents visible growth of a microorganism in an agar or broth dilution susceptibility test.

Current antibiotic susceptibility testing methods are conducted on individual organisms, cultured from a sample prior to susceptibility testing. The Clinical and Laboratory Standards Institute has established antibiotic concentrations specific to the bacterial species being tested and utilized to indicate if the organism is "Sensitive", "Intermediate", or "Resistant" to the tested antibiotic. Testing methods include the "Gold Standard" method of agar dilution, liquid culture dilution, and disk diffusion.

Currently, either broth (liquid) or agar dilution methods may be used to measure quantitatively the in vitro activity of an antimicrobial agent against a given bacterial isolate. To perform the tests, a series of tubes or plates is prepared with a broth or agar medium to which various concentrations of the antimicrobial agents are added. The tubes or plates are then inoculated with a standardized suspension of the test organism. After incubation at 35±4° C., the tests are examined and the MIC is determined. The final result is significantly influenced by methodology, which must be carefully controlled if reproducible results (intra-laboratory and inter-laboratory) are to be achieved.

Currently, isolated colonies of each type of organism that may be pathogenic are selected from primary agar plates and tested individually for susceptibility. Identification procedures are often performed at the same time. It is currently recommended that mixtures of different types of microorganisms are not tested on the same susceptibility test plate or panel.

The practice of conducting susceptibility tests directly with clinical material (e.g., normally sterile body fluids and tissue) had not been previously recommended, except in clinical emergencies when the direct Gram stain suggests a single pathogen. Testing labs were cautioned that when testing has been carried out directly with the clinical material, the results should be reported as preliminary, and the susceptibility test repeated using the standardized methodology with isolated microorganisms. The disclosed methods are thus different than the currently accepted methodology.

While the agar dilution method is considered the gold standard, it is rarely used due to a high labor, materials, and space requirements. This method requires the preparation of petri dishes containing solid agar with growth medium and antibiotic. Separate petri dishes are prepared consisting of different antibiotic concentrations for each of the antibiotics being tested on each bacterial species. For an initial panel of 12 antibiotics, this translates to 45 separate petri dishes for each species. Subsequent to obtaining isolated single organisms (obtained from an overnight incubation on a bacterial species identification plate), the organisms are plated on each of the agar plates and incubated overnight. A microbiologist then visually inspects and documents if the bacteria grew on each of the antibiotic-containing agar plates.

More commonly, the disk diffusion method is currently used wherein the isolated single organisms are plated on growth medium-containing petri dishes and antibiotic impregnated filter paper discs are placed on the agar plate. If the antibiotic, which diffuses into the agar, stops the bacteria from growing, or kills the bacteria, there is a zone of no growth around the disc where the bacteria were present. This is called a zone of inhibition. By measuring the sizes of the zone of inhibition, MIC, sensitivity, and resistance are determined. However, this method requires depositing the bacteria uniformly across the culture plate. Larger inhibition zones correlate with lower MIC.

Also commonly used is the broth microdilution method wherein the isolated single organisms are inoculated into liquid growth medium and antibiotic solution at varying concentrations. If the antibiotic stops the bacteria from growing, or kills the bacteria, the turbidity of the suspension will be much lower or nonexistent compared to turbidity of bacteria inoculated into medium not containing antibiotic. By creating varying concentrations of an antibiotic in liquid medium, MIC, sensitivity, and resistance can be determined.

The methods described herein test the antibiotic sensitivity of the combined microflora of the sample and thus eliminates the need to first isolate individual bacterial species from the sample. The need for separate petri dishes or tubes for each antibiotic or concentration is eliminated by plating the agar growth medium or liquid growth medium with all of the different antibiotic concentrations in different wells of a multi-well plate (e.g., 6-well, 12-well, 24-well, 48-well, 96-well, 384-well plates, or any multi-well plate suitable for this purpose). The labor associated with the visual evaluation of growth is eliminated by use of spectrophotometer analysis. For the method utilizing agar medium, following overnight incubation, an aqueous solution is placed in each of the wells of the multi-well plates and incubated to allow bacterial colonies growing on the surface of the agar to pass into a suspension. Manual agitation may be used to aid this process and the aqueous solution containing any bacteria that may have grown on the agar plate is transferred to a fresh multi-well plate for spectrophotometric analysis. For the method utilizing liquid medium, the suspensions arrayed in the multi-well plate are applied to spectrophotometric analysis without transferring to a new multi-well plate. The $OD_{600}$ measurements are taken to measure bacterial growth. A simple threshold is utilized to indicate if bacteria are present or absent at a given antibiotic concentration.

The present methods are conducted using a plurality of antibiotics selected from the large number available to treat patients. Antibiotics (also referred to as anti-microbial agents or anti-bacterial agents) include, but are not limited to, penicillins, tetracyclines, cephalosporins, quninolones, lincomycins, macrolides, sulronamides, glycopeptide antibiotics, aminoglycosides, carbapenems, ansamycins, lipopeptides, monobactams, nitrofurans, oxaxolidinones, and polypeptides.

Penicillin antibiotics include, but are not limited to, penicillin, methicillin, amoxicillin, ampicillin, flucloxacillin, penicillin G, penicillin V, carbenicillin, piperacillin, ticarcillin, oxacillin, dicloxacillin, azlocillin, cloxacillin, mezlocillin, temocillin, and nafcillin. Additionally, penicillin antibiotics are often used in combination with beta-lactamase inhibitors to provide broader spectrum activity; these combination antibiotics include amoxicillin/clavulanate, ampicillin/sulbactam, piperacillin/tazobactam, and clavulanate/ticarcillin.

Tetracycline antibiotics include, but are not limited to, tetracycline, doxycycline, demeclocycline, minocycline, and oxytetracycline.

Cephalosporin antibiotics include, but are not limited to, cefadroxil, cephradine, cefazolin, cephalexin, cefepime, ceftaroline, loracarbef, cefotetan, cefuroxime, cefprozil, cefoxitin, cefaclor, ceftibuten, cetriaxone, cefotaxime, cefpodoxime, cefdinir, cefixime, cefditoren, ceftizoxime, cefoperazone, cefalotin, cefamanadole, ceftaroline fosamil, cetobiprole, and ceftazidime. Cephalosporin antibiotics are often used in combination with beta-lactamase inhibitors to provide broader spectrum activity; these combination antibiotics include, but are not limited to, avibactam/ceftazidime and ceftolozane/tazobactam.

Quinolone antibiotics include, but are not limited to, lomefloxacin, ofloxacin, norfloxacin, gatifloxacin, ciprofloxacin, moxifloxacin, levofloxacin, gemifloxacin, cinoxacin, nalidixic acid, trovaloxacin, enoxacin, grepafloxacin, temafloxacin, and sparfloxacin.

Lincomycin antibiotics include, but are not limited to, clindamycin and lincomycin.

Macrolide antibiotics include, but are not limited to, azithromycin, clarithromycin, erythromycin, telithromycin, dirithromycin, roxithromycin, troleandomycin, spiramycin, and fidaxomycin.

Sulfonamide antibiotics include, but are not limited to, sulfamethoxazole, sulfasalazine, mafenide, sulfacetamide, sulfadiazine, silver sufadiazine, sulfadimethoxine, sulfanilimide, sulfisoxazole, sulfonamidochrysoidine, and sulfisoxazole. Sulfonamide antibiotics are often used in combination with trimethoprim to improve bactericidal activity.

Glycopeptide antibiotics include, but are not limited to, dalbavancin, oritavancin, telavancin, teicoplanin, and vancomycin.

Aminoglycoside antibiotics include, but are not limited to, paromomycin, tobramycin, gentamicin, amikacin, kanamycin, neomycin, netilmicin, streptomycin, and spectinomycin.

Carbapenem antibiotics include, but are not limited to, imipenem, meropenem, doripenem, ertapenem, and imipenem/cilastatin.

Ansamycin antibiotics include, but are not limited to, geldanamycin, herbimycin, and rifaximin.

Lipopeptide antibiotics include, but are not limited to, daptomycin.

Monobactam antibiotics include, but are not limited to, aztreonam.

Nitrofuran antibiotics include, but are not limited to furazolidone and nitrofurantoin.

Oxaxolidinone antibiotics include, but are not limited to, linezolid, posizolid, radezolid, and torezolid.

Polypeptide antibiotics include, but are not limited to, bacitracin, colistin, and polymyxin B.

Other antibiotics which are not part of any of the above-mentioned groups include, but are not limited to, clofazimine, dapsone, capreomycin, cycloserine, ethambutol, ethionamide, isoniazid, pyrazinamide, rifampicin, rifabutin, rifapentine, streptomycin, arsphenamide, chloramphenicol, fosfomycin, fusidic acid, metronidazole, mupirocin, platensimycin, quinupristin/dalfopristin, thiamphenicol, tigecycline, tinidazole, and trimethoprim.

In some embodiments, the suspected infection is a urinary tract infection and the antibiotic is one or more of ciprofloxacin, levofloxacin, TMP/SMX, ceftriaxone, fluoroquinolone, ciprofloxacin, an aminoglycoside (e.g., gentamicin 5 mg/kg/day), amoxicillin, linezolid, vancomycin, nitrofurantoin, fosfomycin, pivmecillinam, amoxicillin-clavulanate, ampicillin-sulbactam, piperacillin, piperacillin-tazobactam, cephalexin, cefazolin, cefaclor, cefuroxime, cefotetan, cefotaxime, ceftriaxone, ceftazidime, cefepime, cefixime, cefpodoxime, aztreonam, imipenemb, doripenem, trimethoprim, sulfamethoxazole, gatifloxacin, moxifloxacin, ofloxacin, prulifloxacin, clindamycin, azithromycin, and cephalexin.

In some embodiments, the suspected infection is a prostate infection and the antibiotic is one or more of amoxicillin-clavulanate, ampicillin-sulbactam, ampicillin, piperacillin, piperacillin-tazobactam, cephalexin, cefazolin, cefaclor, cefuroxime, cefotetan, cefotaxime, ceftriaxone, ceftazidime, cefepime, cefixime, cefpodoxime, aztreonam, imipenemb, doripenem, vancomycinb, TMP/SMX, trimethoprim, sulfamethoxazole, nitrofurantoin, ciprofloxacin, gatifloxacin, levofloxacin, moxifloxacin, ofloxacin, prulifloxacin, clindamycin, azithromycin, and clarithromycin.

In some embodiments, the suspected infection is a gastrointestinal infection and the antibiotic is one or more of metronidazole, vancomycin, fidaxomicin, nitazoxanide, metronidazole, nitazoxanide, azithromycin, ciprofloxacin, doxycycline, TMP/SMX, fidaxomicin, and tinidazole.

In some embodiments, the suspected infection is a pulmonary infection and the antibiotic is one or more of azithromycin, clarithromycin, cefuroxime, cefpodoxime, cefdinir, ampicillin/clavulanate, ciprofloxacin, levofloxacin, moxifloxacin, gemifloxacin, TMP/SMX, a tetracycline (e.g., doxycycline), amoxicillin, ampicillin, amoxicillin/clavulanate, cefdinir, cefpodoxime proxetil, cefdinir, cefuroxime, levofloxacin, moxifloxacin, aztreonam lysine, colistin, tobramycin, amikacin, piperacillin-tazobactam, and vancomycin.

In some embodiments, the suspected infection is a central nervous system infection and the antibiotic is one or more of penicillin, ampicillin, gentamicin, cefotaxime, cefepime, ceftriaxone, vancomycin, moxifloxacin, gemifloxacin, gatifloxacin, garenoxacin, trovafloxacin, TMP/SMX, aztreonam, meropenem, chloramphenicol, linezolid, rifampin, metronidazole, penicillin G, ceftizoxime, ceftazidime, ampicillin-sulbactam, imipenem, minocycline, and amikacin.

In some embodiments, the suspected infection is a wound infection and the antibiotic is one or more of TMP/SMX, cephalexin, amoxicillin/clavulanate, doxycycline, clindamycin, ticarcillin/clavulanic, piperacillin/tazobactam, ertapenem, vancomycin, cefazolin, ampicillin/sulbactam, cefotaxime, ceftriaxone, metronidazole, and imipenem.

In some embodiments, the suspected infection is a Struvite infection/kidney stone infection and the antibiotic is one or more of ciprofloxacin, levofloxacin, TMP-SMX, ceftriaxone, fluoroquinolone, ciprofloxacin, aminoglycoside (e.g., gentamicin 5 mg/kg/day), amoxicillin, linezolid, cancomycin, nitrofurantoin, fosfomycin, pivmecillinam, amoxicillin-clavulanate, ampicillin-sulbactam, piperacillin, piperacillin-tazobactam, cephalexin, cefazolin, cefaclor, cefuroxime, cefotetan, cefotaxime, ceftriaxone, ceftazidime, cefepime, cefixime, cefpodoxime, aztreonam, imipenemb, doripenem, TMP/SMX, trimethoprim, sulfamethoxazole, gatifloxacin, moxifloxacin, ofloxacin, prulifloxacin, clindamycin, azithromycin, and cephalexin.

In some embodiments, the suspected infection is a nail, skin, paronychia infection and the antibiotic are one or more of ampicillin, TMP/SMX, cephalexin, clindamycin, amoxicillin/clavulanate, doxycycline, clindamycin, ticarcillin/clavulanic, piperacillin/tazobactam, ertapenem, vancomycin, cefazolin, ampicillin/sulbactam, cefotaxime, ceftriaxone, metronidazole, and imipenem.

In some embodiments, the suspected infection is an ear, nose, and throat infection and the antibiotic is one or more of azithromycin, clarithromycin, cefuroxime, cefpodoxime, cefdinir, ampicillin/clavulanate, ciprofloxacin, levofloxacin, moxifloxacin, gemifloxacin, TMP/SMX, a tetracycline (e.g., doxycycline), amoxicillin, ampicillin, amoxicillin/clavulanate, cefdinir, cefpodoxime proxetil, cefdinir, cefuroxime, levofloxacin, moxifloxacin, aztreonam lysine, colistin, tobramycin, amikacin, tobramycin, oflaxacin, doxycycline, penicillin V, piperacillin-tazobactam, and vancomycin.

In some embodiments, the suspected infection is a pre-surgical/surgical site infection and the antibiotic is one or more of cefazolin, cefuroxime, cefazolin, cefuroxime, cefazolin, cefoxitin, cefotetan, ceftriaxone, ampicillin-sulbactam, cefotetan, metronidazole, neomycin sulfate, erythromycin, ertapenem, fluoroquinolone, TMP/SMX, ampicillin, aztreonam, ciprofloxacin, clindamycin, ertapenem, fluconazole, gentamicin, levofloxacin, moxifloxacin, piperacillin-tazobactam, vancomycin, erythromycin, metronidazole, and neomycin.

Additionally, the scope of the presently disclosed methods encompasses the inclusion of antibiotics not yet known, or not yet approved by regulatory authorities. The presently claimed assay can be performed with any anti-bacterial agent and is not limited to the antibiotics disclosed herein.

Now, turning to the disclosed methods, samples are collected from subjects according to standard collection protocols in sterile containers and are transported to the testing facility.

The preparation of the antibiotic resistance (ABR) testing plates involves two steps. First is preparation of antibiotic solutions and the second is preparation of the bacterial growth medium plate. The antibiotics to be tested for any given sample include antibiotics known to be useful for treating the tissue having the suspected infection, or any antibiotics requested by a medical or laboratory professional having knowledge of the particular patient sample. It is anticipated that most assays will be performed with a standard panel of antibiotics based on the type and location of infection suspected by a medical professional. In some embodiments, the standard panel of antibiotics comprises nitrofurantoin, ciprofloxacin, meropenem, ceftriaxone, trimethoprim/sulfamethoxazole, piperacillin/tazobactam, levofloxacin, cefoxitin, tetracycline, ampicillin/sulbactam, ampicillin, and vancomycin. However, patients with known antibiotic allergies or sensitivities, or with a history of antibiotic resistance, may require customized panels of antibiotics. The assay can be performed simultaneous with an unlimited number of antibiotics.

Antibiotic stock solutions are prepared using diluents suitable for each antibiotic and then 10× solutions are prepared and stored in multi-well plates to allow efficient transfer to testing plates. Each antibiotic is tested at at least two concentrations. In some embodiments, three concentrations, four concentrations, five concentrations, six concentrations, seven concentrations, eight concentrations, nine concentrations, or ten concentrations of an antibiotic, or antibiotic combination, are included in the assay. Typically serial dilutions of the antibiotics are prepared wherein each dilution represents half the concentration of the higher concentration. The 10× antibiotic solutions are stored in the multi-well plate according to a plate plan established for the antibiotic panel chosen for the assay. Exemplary plate plans are depicted in the Antibiotic Source Plates in FIG. 1 and FIG. 2. Antibiotic stocks and 10× solutions are stored at 2-8° C. until needed.

The ABR testing plates are multi-well plates (e.g., 6-well, 12-well, 24-well, 48-well, 96-well, 384-well plates, or any multi-well plate suitable for this purpose) capable of containing bacterial growth medium and culturing bacteria. In some embodiments, the plates are 96-well plates. In some embodiments, sterile agar-bacterial growth medium is dispensed into each well of the plate. Exemplary agar-bacterial growth medium include, but are not limited to Mueller-Hinton agar, blood agar, trypticase soy agar, etc. After the agar has solidified at room temperature, 1/10 volume (of bacterial growth medium) of 10× antibiotic solution is added to each well of the test plate according to the pre-determined plate plan. After the antibiotics have been introduced to the bacterial growth medium, the plates are allowed to rest for at least one hour. For long-term storage, the antibiotic-containing ABR plates are stored at 2-8° C. In some embodiments, sterile liquid broth bacterial growth medium mixed with sample is dispensed into each well of the plate containing 1/10 volume (of bacterial growth medium) of 10× antibiotic solution arrayed according to a pre-determined plate plan. Multi-well plates containing 1/10 volume (of final well volume of bacterial growth medium and antibiotic solution) are stored at 2-8° C. for later use or long-term storage.

Samples for the disclosed antibiotic resistance testing may be optionally diluted in sterile aqueous solution or mixed with bacterial growth medium. In some embodiments, a volume of sample for the disclosed antibiotic resistance testing are first mixed with a growth medium and incubated for 0-24 hours at an incubation temperature of 35±4° C. The samples are then diluted with saline and then mixed with growth medium and added to room temperature ABR testing plates at 9/10 volume of each well in the multi-well plate. In some embodiments, samples are added to room temperature ABR plates at 1/20 volume of bacterial growth medium present in the well. A single patient specimen is used for each ABR plate. If multiple patient specimens are to be tested, each specimen is assayed in its own plate. Once inoculated, the plates are covered and incubated to encourage bacterial growth. Embodiments where a single sample is assayed using more than one plate are also within the scope of the present method.

The plates can be used to culture either anaerobic or aerobic bacteria. For culture of anaerobic bacteria, the plates are incubated at a temperature and in a reduced-oxygen environment to encourage growth of anaerobic bacteria. For culture of aerobic bacteria, the plates are incubated at a temperature and in an oxygen-containing environment to encourage growth of aerobic bacteria.

The incubation temperature can vary depending on the expected types of bacteria but will most likely be in a range of 35-40° C. The plates containing samples are incubated for 12-48 hours, 12-24 hours, 24-28 hours, 12-36 hours, 14-30 hours, 16-24 hours, 16-20 hours, or 16-18 hours, or any range bounded by these numbers.

In some embodiments, wherein the assay is performed with an agar-containing medium, after incubation, bacteria present in each well are recovered by resuspension in an aqueous liquid. Suitable liquids include, but are not limited to, water, saline, culture medium, etc. The aqueous liquid should be sterile, or at least free from bacterial growth. A volume of liquid equal to 100% of the volume of bacterial growth medium is carefully added to the wells of the ABR plate and allowed to sit for at least 30 minutes. In some embodiments, the plates are allowed to sit for 35 minutes, 40 minutes, 45 minutes, 50 minutes, or 60 minutes. The resulting suspension is then carefully removed from each well into individual wells of a clean multi-well plate according to the predetermined plate plan. The plates are optionally agitated to cause mixing of the bacteria with the liquid prior to removal of the suspension. In some embodiments wherein the assay is performed using liquid growth medium, the multi-well plate will be applied to $OD_{600}$ measurement immediately after incubation.

The multi-well plate containing the bacteria-containing suspension is then read in a spectrophotometer. The optical density of the recovered liquid is measured at $OD_{600}$ multiple times to correct for uneven distribution of bacteria particles in the suspension. In some embodiments, the plates are read one time, two times, three times, four times, five times, six times, seven times, or eight times. The multiple plate reads occur in sequence without allowing the suspension to settle in the wells.

The multiple $OD_{600}$ of each well are averaged to provide an accurate quantitation of bacteria present in each well under the specific conditions. Each well's average $OD_{600}$ is then adjusted for background by subtracting the average $OD_{600}$ measurements of a well where no bacteria could grow to yield a blanked value. In some embodiments, this no-growth well contains a blend of antibiotics (AB-blend). In some embodiments, this no-growth well contains sodium azide (Na-Azide). The blanked value is representative of the ability of bacteria to grow in the presence of the particular antibiotic in the well.

The blanked results are then converted into a "resistance" (R) or "sensitive" (S) score based on a threshold value. $OD_{600}$ measurements greater than or equal to the threshold are interpreted as resistant, while measurements below the threshold are interpreted as sensitive.

In some embodiments, the threshold value is for a agar-containing medium. In some embodiments, a threshold value has been determined at 0.010 to 1.000, 0.010-0.090, 0.015 to 0.035, or 0.020 to 0.030 based on correlations to a standard reference method. In some embodiments, the threshold value as been determined at about 0.010, about 0.015, about 0.020, about 0.025, about 0.030, about 0.035, about 0.040, about 0.045, about 0.050, about 0.055, about 0.060, about 0.065, about 0.070, about 0.075, about 0.080, about 0.085, or about 0.090 based on correlations to a standard reference method. In some embodiments, a threshold value has been determined at 0.025 based on correlations to a standard reference method.

In some embodiments, the threshold value is for a liquid medium. In some embodiments, a threshold value has been determined at 0.010-1.000, 0.020-0.090, 0.050-0.080, 0.055 to 0.075, or 0.060 to 0.070 based on correlation to a consensus score between two standard reference methods. In some embodiments, the threshold value as been determined at about 0.010, about 0.015, about 0.020, about 0.025, about 0.030, about 0.035, about 0.040, about 0.045, about 0.050, about 0.055, about 0.060, about 0.065, about 0.070, about 0.075, about 0.080, about 0.085, about 0.090, or about 0.095 based on correlation to a consensus score between two standard reference methods. In some embodiments, a threshold value has been determined at 0.065 based on correlation to a consensus score between two standard reference methods.

In other embodiments, any adjusted $OD_{600}$ measurement greater than blank $OD_{600}$ measurement can be determined as indicative of bacterial growth and applied as a threshold value by correlation to a standard reference method or combination of reference methods.

Minimal inhibitory concentrations for each effective antibiotic are then calculated based on the sensitivity or resistance of the culture at the multiple antibiotic concentrations.

Results of the antibiotic resistance assay disclosed herein are transmitted to the appropriate medical professional who then has the option of prescribing an antibiotic, or antibiotics, shown to be active against the patient's infection, changing the antibiotic to a more effective antibiotic, or ordering additional testing.

EXAMPLES

Example 1. Antibiotic Resistance (ABR) Assay Utilizing Agar-Containing Medium

Urine samples suitable for processing with this assay are collected, transported, and stored using BD Vacutainer (gray top) tubes or other suitable leak-proof sterile container. Urine samples may be held at room temperature for 48 hours before test results are compromised.

Antibiotics not received in ready-made solutions were dissolved in appropriate diluent and according to their individual solubility at 10× the concentration desired in the assay as antibiotic stocks. Antibiotic stocks are stored at 2-8° C. and protected from direct sunlight. Prepared antibiotic stock solutions were aliquoted into a 96-deep well plate (Thermo Fisher Scientific) to form an Antibiotic Source Plate, as shown in FIG. 1 and identified by antibiotic name and concentration (µg/mL; 10× final concentration). Antibiotics include in this assay were nitrofurantoin, ciprofloxacin, meropenem, ceftriaxone, trimethoprim, sulfamethoxazole, piperacillin, tazobactam, levofloxacin, cefoxitin, tetracycline, ampicillin, sulbactam, and vancomycin, either singly or in combination. One well was designated AB-blend which contained a combination of antibiotics to ensure there was no bacterial growth.

One hundred microliters of Mueller-Hinton agar medium was aliquoted into each appropriate well position of a 96-well microplate (VIS 96/F-PS, Eppendorf). The medium was allowed to solidify at room temperature for at least 10 min.

The antibiotics (10 µL) at various concentrations were then aliquoted into desired wells from the Antibiotic Source Plate. After the antibiotics were introduced to the agar medium, the ABR microplates were allowed to sit for at least 1 hr before use. If long-term storage is required, ABR microplates containing antibiotic-infuse agar are stored at 2-8° C. in the dark.

At the time of testing, urine samples were diluted 1:20 in sterile saline and vortexed. Each patient sample utilized a single ABR microplate. Five microliters of diluted patient sample were added to each well of the room temperature microplate, the plate was sealed and incubated for 16-18 hr at 37° C.

After incubation, the plate was removed from the incubator and carefully uncovered. Two-hundred microliters of deionized water were added to each well to suspend cells present above the agar and the plates incubated at room temperature for 30 min. After 30 min, 100 µl from each well was removed to a new plate and the $OD_{600}$ was determined in a spectrophotometer. Five separate reads were taken of each plate and a mean $OD_{600}$ measurement calculated.

Controls are depicted in Table 1.

TABLE 1

| Controls | |
| --- | --- |
| Control Name | Control Conditions |
| No-antibiotic control | Any well containing medium that is not infused with antibiotics to ensure viability of bacterial cells present in patient urine samples and included in each plate. If the no-antibiotic control for any given patient does not yield growth, a secondary test is performed using the same patient sample without dilution. |
| Negative control plate | Microplate containing antibiotic-infused agar medium without addition of patient sample or cultured bacterial organisms to ensure non-contamination of reagents. |
| AB-Blend | One or more wells containing a combination of antibiotics to ensure there is no bacterial growth |

Raw data collected from the plate is depicted in Table 2. Data in spreadsheet form was arranged as "Well Position" adjacent to its corresponding "Mean" OD.

TABLE 2

| Raw Data | |
| --- | --- |
| Well | Mean |
| A7 | 0.6960 |
| A8 | 0.0388 |
| A9 | 0.0744 |
| A10 | 0.0385 |
| A11 | 0.0477 |
| A12 | 0.4550 |
| B7 | 0.0387 |
| B8 | 0.0390 |
| B9 | 0.0412 |
| B10 | 0.4250 |
| B11 | 0.0449 |
| B12 | 0.4880 |
| C7 | 0.0386 |
| C8 | 0.0385 |
| C9 | 0.0445 |
| C10 | 0.4296 |
| C11 | 0.0401 |
| C12 | 0.5222 |
| D7 | 0.0392 |
| D8 | 0.5372 |
| D9 | 0.0432 |
| D10 | 0.4377 |
| D11 | 0.0392 |
| D12 | 0.4824 |
| E7 | 0.0408 |
| E8 | 0.5029 |
| E9 | 0.0405 |
| E10 | 0.4918 |
| E11 | 0.0389 |
| E12 | 0.5087 |
| F7 | 0.0414 |
| F8 | 0.2925 |

TABLE 2-continued

Raw Data

| Well | Mean |
|---|---|
| F9 | 0.0392 |
| F10 | 0.4378 |
| F11 | 0.0389 |
| F12 | 0.5307 |
| G7 | 0.0387 |
| G8 | 0.0408 |
| G9 | 0.0391 |
| G10 | 0.0495 |
| G11 | 0.4304 |
| G12 | 0.0384 |
| H7 | 0.0392 |
| H8 | 0.0401 |
| H9 | 0.0386 |
| H10 | 0.0474 |
| H11 | 0.4396 |
| H12 | 0.7874 |

Each well position corresponds to a particular antibiotic at a certain concentration according to the plate plan. Addition of the antibiotic legend is depicted in Table 3.

TABLE 3

| Antibiotic | Well | Mean |
|---|---|---|
| No-antibiotic | A7 | 0.6960 |
| Mero-2 | A8 | 0.0388 |
| Levo-4 | A9 | 0.0744 |
| Ceftria-64 | A10 | 0.0385 |
| Pip/Tazo-64,4 | A11 | 0.0477 |
| Tetra-16 | A12 | 0.4550 |
| Nitro-32 | B7 | 0.0387 |
| Mero-4 | B8 | 0.0390 |
| Levo-8 | B9 | 0.0412 |
| Vanco-2 | B10 | 0.4250 |
| Pip/Tazo-128,4 | B11 | 0.0449 |
| Amp-8 | B12 | 0.4880 |
| Nitro-64 | C7 | 0.0386 |
| Mero-8 | C8 | 0.0385 |
| Ceftria-1 | C9 | 0.0445 |
| Vanco-4 | C10 | 0.4296 |
| Cefox-4 | C11 | 0.0401 |
| Amp-16 | C12 | 0.5222 |
| Nitro-128 | D7 | 0.0392 |
| Amp/Sulb-8,4 | D8 | 0.5372 |
| Ceftria-2 | D9 | 0.0432 |
| Vanco-8 | D10 | 0.4377 |
| Cefox-8 | D11 | 0.0392 |
| Amp-32 | D12 | 0.4824 |
| Cipro-1 | E7 | 0.0408 |
| Amp/Sulb-16,8 | E8 | 0.5029 |
| Ceftria-4 | E9 | 0.0405 |
| Vanco-16 | E10 | 0.4918 |
| Cefox-16 | E11 | 0.0389 |
| TMP/SMX-2,38 | E12 | 0.5087 |
| Cipro-2 | F7 | 0.0414 |
| Amp/Sulb-32,16 | F8 | 0.2925 |
| Ceftria-8 | F9 | 0.0392 |
| Vanco-32 | F10 | 0.4378 |
| Cefox-32 | F11 | 0.0389 |
| TMP/SMX-4,76 | F12 | 0.5307 |
| Cipro-4 | G7 | 0.0387 |
| Levo-1 | G8 | 0.0408 |
| Ceftria-16 | G9 | 0.0391 |
| Pip/Tazo-16,4 | G10 | 0.0495 |
| Tetra-4 | G11 | 0.4304 |
| AB-Blend | G12 | 0.0384 |
| Mero-1 | H7 | 0.0392 |
| Levo-2 | H8 | 0.0401 |
| Ceftria-32 | H9 | 0.0386 |
| Pip/Tazo-32,4 | H10 | 0.0474 |
| Tetra-8 | H11 | 0.4396 |
| empty | H12 | 0.7874 |

Once the antibiotic legend was placed adjacent to the appropriate well, the data was rearranged by sorting like antibiotics together (Table 4).

TABLE 4

| Antibiotic | Well | Mean |
|---|---|---|
| No-antibiotic | A7 | 0.6960 |
| Nitro-32 | B7 | 0.0387 |
| Nitro-64 | C7 | 0.0386 |
| Nitro-128 | D7 | 0.0392 |
| Cipro-1 | E7 | 0.0408 |
| Cipro-2 | F7 | 0.0414 |
| Cipro-4 | G7 | 0.0387 |
| Mero-1 | H7 | 0.0392 |
| Mero-2 | A8 | 0.0388 |
| Mero-4 | B8 | 0.0390 |
| Mero-8 | C8 | 0.0385 |
| Amp/Sulb-8,4 | D8 | 0.5372 |
| Amp/Sulb-16,8 | E8 | 0.5029 |
| Amp/Sulb-32,16 | F8 | 0.2925 |
| Levo-1 | G8 | 0.0408 |
| Levo-2 | H8 | 0.0401 |
| Levo-4 | A9 | 0.0744 |
| Levo-8 | B9 | 0.0412 |
| Ceftria-1 | C9 | 0.0445 |
| Ceftria-2 | D9 | 0.0432 |
| Ceftria-4 | E9 | 0.0405 |
| Ceftria-8 | F9 | 0.0392 |
| Ceftria-16 | G9 | 0.0390 |
| Ceftria-32 | H9 | 0.0386 |
| Ceftria-64 | A10 | 0.0385 |
| Vanco-2 | B10 | 0.4250 |
| Vanco-4 | C10 | 0.4296 |
| Vanco-8 | D10 | 0.4377 |
| Vanco-16 | E10 | 0.4918 |
| Vanco-32 | F10 | 0.4378 |
| Pip/Tazo-16,4 | G10 | 0.0495 |
| Pip/Tazo-32,4 | H10 | 0.0474 |
| Pip/Tazo-64,4 | A11 | 0.0477 |
| Pip/Tazo-128,4 | B11 | 0.0449 |
| Cefox-4 | C11 | 0.0401 |
| Cefox-8 | D11 | 0.0392 |
| Cefox-16 | E11 | 0.0389 |
| Cefox-32 | F11 | 0.0389 |
| Tetra-4 | G11 | 0.4304 |
| Tetra-8 | H11 | 0.4396 |
| Tetra-16 | A12 | 0.4550 |
| Amp-8 | B12 | 0.4880 |
| Amp-16 | C12 | 0.5222 |
| Amp-32 | D12 | 0.4824 |
| TMP/SMX-2,38 | E12 | 0.5087 |
| TMP/SMX-4,76 | F12 | 0.5307 |
| AB-Blend | G12 | 0.0384 |
| empty | H12 | 0.7874 |

The raw data was then "blanked" using the measurement obtained from the AB-Blend well, as depicted in Table 5.

TABLE 5

| Antibiotic | Well | Mean | Blanked |
|---|---|---|---|
| No-antibiotic | A7 | 0.6960 | 0.6576 |
| Nitro-32 | B7 | 0.0387 | 0.0003 |
| Nitro-64 | C7 | 0.0386 | 0.0002 |
| Nitro-128 | D7 | 0.0392 | 0.0008 |
| Cipro-1 | E7 | 0.0408 | 0.0024 |
| Cipro-2 | F7 | 0.0414 | 0.0030 |
| Cipro-4 | G7 | 0.0387 | 0.0003 |
| Mero-1 | H7 | 0.0392 | 0.0008 |
| Mero-2 | A8 | 0.0388 | 0.0004 |
| Mero-4 | B8 | 0.0390 | 0.0006 |
| Mero-8 | C8 | 0.0385 | 0.0001 |
| Amp/Sulb-8,4 | D8 | 0.5372 | 0.4988 |
| Amp/Sulb-16,8 | E8 | 0.5029 | 0.4646 |
| Amp/Sulb-32,16 | F8 | 0.2925 | 0.2541 |
| Levo-1 | G8 | 0.0408 | 0.0024 |

TABLE 5-continued

| Antibiotic | Well | Mean | Blanked |
|---|---|---|---|
| Levo-2 | H8 | 0.0401 | 0.0017 |
| Levo-4 | A9 | 0.0744 | 0.0360 |
| Levo-8 | B9 | 0.0412 | 0.0028 |
| Ceftria-1 | C9 | 0.0445 | 0.0061 |
| Ceftria-2 | D9 | 0.0432 | 0.0048 |
| Ceftria-4 | E9 | 0.0405 | 0.0021 |
| Ceftria-8 | F9 | 0.0392 | 0.0008 |
| Ceftria-16 | G9 | 0.0391 | 0.0007 |
| Ceftria-32 | H9 | 0.0386 | 0.0002 |
| Ceftria-64 | A10 | 0.0385 | 0.0001 |
| Vanco-2 | B10 | 0.4250 | 0.3866 |
| Vanco-4 | C10 | 0.4296 | 0.3912 |
| Vanco-8 | D10 | 0.4377 | 0.3993 |
| Vanco-16 | E10 | 0.4918 | 0.4534 |
| Vanco-32 | F10 | 0.4378 | 0.3994 |
| Pip/Tazo-16,4 | G10 | 0.0495 | 0.0111 |
| Pip/Tazo-32,4 | H10 | 0.0474 | 0.0090 |
| Pip/Tazo-64,4 | A11 | 0.0477 | 0.0093 |
| Pip/Tazo-128,4 | B11 | 0.0449 | 0.0065 |
| Cefox-4 | C11 | 0.0401 | 0.0017 |
| Cefox-8 | D11 | 0.0392 | 0.0008 |
| Cefox-16 | E11 | 0.0389 | 0.0005 |
| Cefox-32 | F11 | 0.0389 | 0.0005 |
| Tetra-4 | G11 | 0.4304 | 0.3920 |
| Tetra-8 | H11 | 0.4396 | 0.4012 |
| Tetra-16 | A12 | 0.4550 | 0.4166 |
| Amp-8 | B12 | 0.4880 | 0.4496 |
| Amp-16 | C12 | 0.5222 | 0.4838 |
| Amp-32 | D12 | 0.4824 | 0.4440 |
| TMP/SMX-2,38 | E12 | 0.5087 | 0.4703 |
| TMP/SMX-4,76 | F12 | 0.5307 | 0.4923 |
| AB-Blend | G12 | 0.0384 | 0 |
| empty | H12 | 0.7874 | 0.7490 |

To determine whether bacterial organisms present in the patient samples were resistant or sensitive to a particular antibiotic at a certain concentration, blanked OD readings were compared to a threshold $OD_{600}$ of 0.025 (Table 6). Any OD measurement greater than or equal to this threshold was designated Resistant (R) meaning bacterial organisms present in patient sample were resistant to that particular antibiotic at that certain concentration. Any OD measurement less than this threshold was designated Sensitive (S) meaning bacterial organisms present in patient sample were sensitive to that particular antibiotic at that certain concentration.

TABLE 6

| Antibiotic | Well | Mean | Blanked | Result |
|---|---|---|---|---|
| No-antibiotic | A7 | 0.6960 | 0.6576 | R |
| Nitro-32 | B7 | 0.0387 | 0.0003 | S |
| Nitro-64 | C7 | 0.0386 | 0.0002 | S |
| Nitro-128 | D7 | 0.0392 | 0.0008 | S |
| Cipro-1 | E7 | 0.0408 | 0.0024 | S |
| Cipro-2 | F7 | 0.0414 | 0.0030 | S |
| Cipro-4 | G7 | 0.0387 | 0.0003 | S |
| Mero-1 | H7 | 0.0392 | 0.0008 | S |
| Mero-2 | A8 | 0.0388 | 0.0004 | S |
| Mero-4 | B8 | 0.0390 | 0.0006 | S |
| Mero-8 | C8 | 0.0385 | 0.0001 | S |
| Amp/Sulb-8,4 | D8 | 0.5372 | 0.4988 | R |
| Amp/Sulb-16,8 | E8 | 0.5029 | 0.4646 | R |
| Amp/Sulb-32,16 | F8 | 0.2925 | 0.2541 | R |
| Levo-1 | G8 | 0.0408 | 0.0024 | S |
| Levo-2 | H8 | 0.0401 | 0.0017 | S |
| Levo-4 | A9 | 0.0744 | 0.0360 | R |
| Levo-8 | B9 | 0.0412 | 0.0028 | S |
| Ceftria-1 | C9 | 0.0445 | 0.0061 | S |
| Ceftria-2 | D9 | 0.0432 | 0.0048 | S |
| Ceftria-4 | E9 | 0.0405 | 0.0021 | S |
| Ceftria-8 | F9 | 0.0392 | 0.0008 | S |
| Ceftria-16 | G9 | 0.0391 | 0.0007 | S |
| Ceftria-32 | H9 | 0.0386 | 0.0002 | S |
| Ceftria-64 | A10 | 0.0385 | 0.0001 | S |
| Vanco-2 | B10 | 0.4250 | 0.3866 | R |
| Vanco-4 | C10 | 0.4296 | 0.3912 | R |
| Vanco-8 | D10 | 0.4377 | 0.3993 | R |
| Vanco-16 | E10 | 0.4918 | 0.4534 | R |
| Vanco-32 | F10 | 0.4378 | 0.3994 | R |
| Pip/Tazo-16,4 | G10 | 0.0495 | 0.0111 | S |
| Pip/Tazo-32,4 | H10 | 0.0474 | 0.0090 | S |
| Pip/Tazo-64,4 | A11 | 0.0477 | 0.0093 | S |
| Pip/Tazo-128,4 | B11 | 0.0449 | 0.0065 | S |
| Cefox-4 | C11 | 0.0401 | 0.0017 | S |
| Cefox-8 | D11 | 0.0392 | 0.0008 | S |
| Cefox-16 | E11 | 0.0389 | 0.0005 | S |
| Cefox-32 | F11 | 0.0389 | 0.0005 | S |
| Tetra-4 | G11 | 0.4304 | 0.3920 | R |
| Tetra-8 | H11 | 0.4396 | 0.4012 | R |
| Tetra-16 | A12 | 0.4550 | 0.4166 | R |
| Amp-8 | B12 | 0.4880 | 0.4496 | R |
| Amp-16 | C12 | 0.5222 | 0.4838 | R |
| Amp-32 | D12 | 0.4824 | 0.4440 | R |
| TMP/SMX-2,38 | E12 | 0.5087 | 0.4703 | R |
| TMP/SMX-4,76 | F12 | 0.5307 | 0.4923 | R |
| AB-Blend | G12 | 0.0384 | 0 | S |
| empty | H12 | 0.7874 | 0.7490 | R |

In this example, the sample contains bacteria sensitive to nitrofurantoin, ciprofloxacin, meropenem, ceftriaxone, piperacillin/tazobactam, and cefoxitin. The results for levo are equivocal.

The MIC for each drug can then be provided. The minimum inhibitory concentration (MIC) is the minimum test antibiotic concentration to which the sample is sensitive. An exemplary MIC determination for meropenem based on the results above is depicted in Table 7.

TABLE 7

| Mero [1] | Mero [2] | Mero [4] | Mero [8] | MIC | Interpretation |
|---|---|---|---|---|---|
| S | S | S | S | <=1 | S |
| R | S | S | S | <=2 | I |
| R | R | S | S | <=4 | I |
| R | R | R | S | <=8 | I |
| R | R | R | R | >=8 | R |

Example 2. Validation of ABR Assay Utilizing Agar Containing Growth Medium

Accuracy

Accuracy was assessed by comparing the antibiotic resistance results of the test method compared to those obtained for mixed and isolated cultures evaluated by the antibiotic-agar method. A total of 19 bacterial pools (pools consist of 2-4 organisms), 17 isolated organisms, and 9 routinely processed urine samples were tested for resistance to 12 antibiotics. Accuracy was assessed in regards to Specificity (True Negatives), Sensitivity (True Positives), and Overall Accuracy (All Samples). The assay showed good accuracy in all three categories (Table 8).

TABLE 8

| | % Accuracy |
|---|---|
| Overall Accuracy | 96% |
| Specificity | 95% |
| Sensitivity | 96% |

Precision

Inter-assay precision was evaluated by testing three samples from the "Accuracy" sample set over three days. Intra-assay precision was evaluated by testing each of these samples in triplicate in one batch. Precision for each sample was assessed by determining the consensus result of all 5 replicates and then counting the number of replicates that match the consensus. This number was then divided by the sum of all measurements (sum of measurements for all drugs) to determine the % precision. The overall precision was calculated by dividing the sum of all correct matches by the total number of measurements from all samples. The assay demonstrated very good precision (Table 9).

TABLE 9

|  | All Precision Samples |
|---|---|
| Total Matched | 643 |
| Total Measurements | 690 |
| % Match | 93% |

Analytical Sensitivity

Analytic sensitivity, or the limit of detection (LOD), was assessed by determined the lowest bacterial concentration that yielded accurate results. Bacterial concentrations lower than 10,000 cells/mL are not considered positive for UTI and therefore the lowest concentration tested was 10,000 cells/mL. Consistent results (>98%) correlation to the consensus results were obtained at the lowest bacterial concentrations tested. The LOD of this assay was 10,000 cells/mL.

Analytical Specificity

The analytic specificity of this assay was assessed by testing samples at bacterial concentrations of 100,000,000 cells/mL. Such concentrations are not typically observed in routine UTI patient samples but were achieved in saturated overnight bacterial cultures. Assessment of analytic measurement range (AMR) was then performed by testing three samples from the "Accuracy" sample set each diluted as follows: 100,000,000 cells/mL, 1,000,000 cells/mL, 100,000 cells/mL and 10,000 cells/mL. Consistent results (>94%) correlation to the consensus results were obtained at all bacterial concentrations tested. The assay is specific at bacterial concentration up to 100,000,000 cells/mL.

Example 3. Antibiotic Resistance (ABR) Assay Utilizing Liquid Growth Medium

Urine samples suitable for processing with this assay are collected, transported, and stored using BD Vacutainer tubes or other suitable leak-proof sterile containers. Urine samples may be held at room temperature for 48 hours before test results are compromised.

Antibiotics not received in ready-made solutions were dissolved in appropriate solvents and according to their individual solubility to 50× the concentration desired in the assay and stored as antibiotic stocks. Antibiotic stocks are stored at 2-8° C. and protected from direct sunlight. Prepared antibiotic stock solutions were aliquoted into a 96-deep well plate (ThermoFisher Scientific) to form a 50× Antibiotic Source Plate and then diluted 1:5 to form a 10× Antibiotic Source Plate, as shown in FIG. 2 where each well is identified by antibiotic name and concentration (µg/mL; 10× final concentration). Antibiotics included in this assay were amoxicillin, clavulanate, ampicillin, sulbactam, cefaclor, cefazolin, cefepime, cefoxitin, ceftazidime, ceftriaxone, ciprofloxacin, gentamicin, levofloxacin, meropenem, nitrofurantoin, piperacillin, tazobactam, tetracycline, trimethoprim, sulfamethoxazole, and vancomycin, either singly or in combination. One well was assigned sodium azide to ensure no bacterial growth would be observed in that well.

Twenty microliters of each antibiotic solution were aliquoted into the pre-determined wells of a 96-well microplate (VIS 96/F-PS, Eppendorf) from the 10× Antibiotic Source Plate to create ABR testing plates for inoculation. These ABR testing plates were allowed to sit for up to 24 hours before use at 2-8° C. in the dark.

At the time of testing, urine samples were centrifuged to concentrate any bacterial cells and then mixed with liquid Mueller-Hinton medium and incubated for 6-16 hours at 37° C. After this initial incubation, the sample is diluted to 0.5-0.6 McF in saline and then 500 µl of that suspension was added to 29.5 µl of Mueller-Hinton medium. One-hundred and eighty microliters of the diluted sample is then aliquoted to each well of the ABR microplate already containing 10× antibiotic solution, bringing all of the antibiotics to the desired final concentration. The plate is then sealed and incubated for 12-16 hours at 37° C.

After incubation, the plate was removed from the incubator and carefully uncovered and the OD600 was determined for each appropriate well by spectrophotometer. Five separate measurements were taken of each well on a plate and the mean OD600 measurement calculated for each well.

Controls are depicted in Table 10.

TABLE 10

| Controls | |
|---|---|
| Control Name | Control Conditions |
| No-antibiotic control | Any well containing medium that is not infused with antibiotics to ensure viability of bacterial cells present in patient urine samples and included in each plate. If the no-antibiotic control for any given patient does not yield growth, the sample is repeated on the assay and reported as quantity not sufficient if repeat testing still does not yield satisfactory results. |
| Negative control plate | Microplate containing antibiotic-infused agar medium without addition of patient sample or cultured bacterial organisms to ensure non-contamination of reagents. |
| Na Azide | One or more wells containing a dilute concentration of sodium azide to ensure no bacterial growth will occur. |

Raw data collected from the plate is depicted in Table 11. Data in spreadsheet form was arranged as "Well Position" adjacent to its corresponding "Mean" OD.

TABLE 11

| Raw Data | |
|---|---|
| Well | Mean |
| A1 | 0.2217 |
| A2 | 0.0496 |
| A3 | 0.2357 |
| A4 | 0.0421 |
| A5 | 0.0539 |
| A6 | 0.1468 |
| A7 | 0.2457 |
| A8 | 0.0427 |
| B1 | 0.0552 |
| B2 | 0.0413 |
| B3 | 0.2449 |

TABLE 11-continued

Raw Data

| Well | Mean |
|---|---|
| B4 | 0.0419 |
| B5 | 0.0417 |
| B6 | 0.0570 |
| B7 | 0.2607 |
| B8 | 0.0419 |
| C1 | 0.0539 |
| C2 | 0.0414 |
| C3 | 0.2356 |
| C4 | 0.2202 |
| C5 | 0.0419 |
| C6 | 0.2416 |
| C7 | 0.2473 |
| C8 | 0.2332 |
| D1 | 0.0441 |
| D2 | 0.1180 |
| D3 | 0.0504 |
| D4 | 0.2288 |
| D5 | 0.0418 |
| D6 | 0.2427 |
| D7 | 0.2437 |
| D8 | 0.0600 |
| E1 | 0.0423 |
| E2 | 0.0436 |
| E3 | 0.0435 |
| E4 | 0.2348 |
| E5 | 0.1209 |
| E6 | 0.2417 |
| E7 | 0.0615 |
| E8 | 0.0457 |
| F1 | 0.2198 |
| F2 | 0.0431 |
| F3 | 0.0425 |
| F4 | 0.2084 |
| F5 | 0.1016 |
| F6 | 0.2404 |
| F7 | 0.0426 |
| F8 | 0.2604 |
| G1 | 0.1928 |
| G2 | 0.0443 |
| G3 | 0.0431 |
| G4 | 0.2224 |
| G5 | 0.2339 |
| G6 | 0.2323 |
| G7 | 0.0418 |
| G8 | 0.2354 |
| H1 | 0.1556 |
| H2 | 0.2485 |
| H3 | 0.0426 |
| H4 | 0.1596 |
| H5 | 0.2090 |
| H6 | 0.2281 |
| H7 | 0.0437 |
| H8 | 0.2446 |

Each well position corresponds to a particular antibiotic at a certain concentration according to the plate plan. Addition of the antibiotic legend is depicted in Table 12.

TABLE 12

| Antibiotic | Well | Mean |
|---|---|---|
| No-Antibiotic | A1 | 0.2217 |
| Mero-8 | A2 | 0.0496 |
| Ceftriaxone-4 | A3 | 0.2357 |
| Pip/Tazo-16,4 | A4 | 0.0421 |
| Tetra-16 | A5 | 0.0539 |
| Cefazolin-16 | A6 | 0.1468 |
| Ceftazidime-4 | A7 | 0.2457 |
| No-Antibiotic | A8 | 0.0427 |
| Nitro-32 | B1 | 0.0552 |
| Amp/Sulb-8,4 | B2 | 0.0413 |
| Ceftriaxone-8 | B3 | 0.2449 |
| Pip/Tazo-128,4 | B4 | 0.0419 |

TABLE 12-continued

| Antibiotic | Well | Mean |
|---|---|---|
| Amp-8 | B5 | 0.0417 |
| Cefazolin-32 | B6 | 0.0570 |
| Ceftazidime-8 | B7 | 0.2607 |
| No-Antibiotic | B8 | 0.0419 |
| Nitro-128 | C1 | 0.0539 |
| Amp/Sulb-32,16 | C2 | 0.0414 |
| Ceftriaxone-64 | C3 | 0.2356 |
| Cefoxitin-4 | C4 | 0.2202 |
| Amp-16 | C5 | 0.0419 |
| Cefepime-1 | C6 | 0.2416 |
| Ceftazidime-16 | C7 | 0.2473 |
| Cefaclor-8 | C8 | 0.2332 |
| Cipro-1 | D1 | 0.0441 |
| Levo-1 | D2 | 0.1180 |
| Vanco-1 | D3 | 0.0504 |
| Cefoxitin-8 | D4 | 0.2288 |
| Amp-32 | D5 | 0.0418 |
| Cefepime-2 | D6 | 0.2427 |
| Ceftazidime-32 | D7 | 0.2437 |
| Cefaclor-32 | D8 | 0.0600 |
| Cipro-4 | E1 | 0.0423 |
| Levo-2 | E2 | 0.0436 |
| Vanco-2 | E3 | 0.0435 |
| Cefoxitin-32 | E4 | 0.2348 |
| TMP/SMX-2,38 | E5 | 0.1209 |
| Cefepime-4 | E6 | 0.2417 |
| Gentamicin-4 | E7 | 0.0615 |
| Na Azide | E8 | 0.0457 |
| Mero-1 | F1 | 0.2198 |
| Levo-4 | F2 | 0.0431 |
| Vanco-4 | F3 | 0.0425 |
| Tetra-2 | F4 | 0.2084 |
| TMP/SMX-4,76 | F5 | 0.1016 |
| Cefepime-8 | F6 | 0.2404 |
| Gentamicin-16 | F7 | 0.0426 |
| No-Antibiotic | F8 | 0.2604 |
| Mero-2 | G1 | 0.1928 |
| Levo-8 | G2 | 0.0443 |
| Vanco-16 | G3 | 0.0431 |
| Tetra-4 | G4 | 0.2224 |
| Cefazolin-2 | G5 | 0.2339 |
| Cefepime-16 | G6 | 0.2323 |
| Amox/Clav-8,4 | G7 | 0.0418 |
| No-Antibiotic | G8 | 0.2354 |
| Mero-4 | H1 | 0.1556 |
| Ceftriaxone-1 | H2 | 0.2485 |
| Vanco-32 | H3 | 0.0426 |
| Tetra-8 | H4 | 0.1596 |
| Cefazolin-8 | H5 | 0.2090 |
| Cefepime-32 | H6 | 0.2281 |
| Amox/Clav-32,16 | H7 | 0.0437 |
| No Antibiotic | H8 | 0.2446 |

With antibiotic legend placed adjacent to the appropriate well, the data was rearranged by sorting like antibiotics together (Table 13).

TABLE 13

| Antibiotic | Well | Mean |
|---|---|---|
| Na Azide | E8 | 0.0457 |
| No-Antibiotic | A1 | 0.2217 |
| No-Antibiotic | F8 | 0.2604 |
| No-Antibiotic | G8 | 0.2354 |
| No-Antibiotic | H8 | 0.2446 |
| Amox/Clav-8,4 | G7 | 0.0418 |
| Amox/Clav-32,16 | H7 | 0.0437 |
| Amp-8 | B5 | 0.0417 |
| Amp-16 | C5 | 0.0419 |
| Amp-32 | D5 | 0.0418 |
| Amp/Sulb-8,4 | B2 | 0.0413 |
| Amp/Sulb-32,16 | C2 | 0.0414 |
| Cefaclor-8 | C8 | 0.2332 |
| Cefaclor-32 | D8 | 0.0600 |
| Cefazolin-2 | G5 | 0.2339 |

TABLE 13-continued

| Antibiotic | Well | Mean |
| --- | --- | --- |
| Cefazolin-8 | H5 | 0.2090 |
| Cefazolin-16 | A6 | 0.1468 |
| Cefazolin-32 | B6 | 0.0570 |
| Cefepime-1 | C6 | 0.2416 |
| Cefepime-2 | D6 | 0.2427 |
| Cefepime-4 | E6 | 0.2417 |
| Cefepime-8 | F6 | 0.2404 |
| Cefepime-16 | G6 | 0.2323 |
| Cefepime-32 | H6 | 0.2281 |
| Cefoxitin-4 | C4 | 0.2202 |
| Cefoxitin-8 | D4 | 0.2288 |
| Cefoxitin-32 | E4 | 0.2348 |
| Ceftazidime-4 | A7 | 0.2457 |
| Ceftazidime-8 | B7 | 0.2607 |
| Ceftazidime-16 | C7 | 0.2473 |
| Ceftazidime-32 | D7 | 0.2437 |
| Ceftriaxone-1 | H2 | 0.2485 |
| Ceftriaxone-4 | A3 | 0.2357 |
| Ceftriaxone-8 | B3 | 0.2449 |
| Ceftriaxone-64 | C3 | 0.2356 |
| Cipro-1 | D1 | 0.0441 |
| Cipro-4 | E1 | 0.0423 |
| No-Antibiotic | A8 | 0.0427 |
| No-Antibiotic | B8 | 0.0419 |
| Gentamicin-4 | E7 | 0.0615 |
| Gentamicin-16 | F7 | 0.0426 |
| Levo-1 | D2 | 0.1180 |
| Levo-2 | E2 | 0.0436 |
| Levo-4 | F2 | 0.0431 |
| Levo-8 | G2 | 0.0443 |
| Mero-1 | F1 | 0.2198 |
| Mero-2 | G1 | 0.1928 |
| Mero-4 | H1 | 0.1556 |
| Mero-8 | A2 | 0.0496 |
| Nitro-32 | B1 | 0.0552 |
| Nitro-128 | C1 | 0.0539 |
| Pip/Tazo-16,4 | A4 | 0.0421 |
| Pip/Tazo-128,4 | B4 | 0.0419 |
| Tetra-2 | F4 | 0.2084 |
| Tetra-4 | G4 | 0.2224 |
| Tetra-8 | H4 | 0.1596 |
| Tetra-16 | A5 | 0.0539 |
| TMP/SMX-2,38 | E5 | 0.1209 |
| TMP/SMX-4,76 | F5 | 0.1016 |
| Vanco-1 | D3 | 0.0504 |
| Vanco-2 | E3 | 0.0435 |
| Vanco-4 | F3 | 0.0425 |
| Vanco-16 | G3 | 0.0431 |
| Vanco-32 | H3 | 0.0426 |

The raw data was then "blanked" using the measurement obtained from the Na-Azide well, as depicted in Table 14.

TABLE 14

| Antibiotic | Well | Mean | Blanked |
| --- | --- | --- | --- |
| Na Azide | E8 | 0.0457 | 0 |
| No-Antibiotic | A1 | 0.2217 | 0.1760 |
| No-Antibiotic | F8 | 0.2604 | 0.2147 |
| No-Antibiotic | G8 | 0.2354 | 0.1897 |
| No-Antibiotic | H8 | 0.2446 | 0.1989 |
| Amox/Clav-8,4 | G7 | 0.0418 | −0.0039 |
| Amox/Clav-32,16 | H7 | 0.0437 | −0.0020 |
| Amp-8 | B5 | 0.0417 | −0.0040 |
| Amp-16 | C5 | 0.0419 | −0.0038 |
| Amp-32 | D5 | 0.0418 | −0.0039 |
| Amp/Sulb-8,4 | B2 | 0.0413 | −0.0044 |
| Amp/Sulb-32,16 | C2 | 0.0414 | −0.0043 |
| Cefaclor-8 | C8 | 0.2332 | 0.1875 |
| Cefaclor-32 | D8 | 0.0600 | 0.0143 |
| Cefazolin-2 | G5 | 0.2339 | 0.1882 |
| Cefazolin-8 | H5 | 0.2090 | 0.1633 |
| Cefazolin-16 | A6 | 0.1468 | 0.1011 |
| Cefazolin-32 | B6 | 0.0570 | 0.0113 |
| Cefepime-1 | C6 | 0.2416 | 0.1959 |
| Cefepime-2 | D6 | 0.2427 | 0.1970 |
| Cefepime-4 | E6 | 0.2417 | 0.1960 |
| Cefepime-8 | F6 | 0.2404 | 0.1947 |
| Cefepime-16 | G6 | 0.2323 | 0.1866 |
| Cefepime-32 | H6 | 0.2281 | 0.1824 |
| Cefoxitin-4 | C4 | 0.2202 | 0.1745 |
| Cefoxitin-8 | D4 | 0.2288 | 0.1831 |
| Cefoxitin-32 | E4 | 0.2348 | 0.1891 |
| Ceftazidime-4 | A7 | 0.2457 | 0.2000 |
| Ceftazidime-8 | B7 | 0.2607 | 0.2150 |
| Ceftazidime-16 | C7 | 0.2473 | 0.2016 |
| Ceftazidime-32 | D7 | 0.2437 | 0.1980 |
| Ceftriaxone-1 | H2 | 0.2485 | 0.2028 |
| Ceftriaxone-4 | A3 | 0.2357 | 0.1900 |
| Ceftriaxone-8 | B3 | 0.2449 | 0.1992 |
| Ceftriaxone-64 | C3 | 0.2356 | 0.1899 |
| Cipro-1 | D1 | 0.0441 | −0.0016 |
| Cipro-4 | E1 | 0.0423 | −0.0034 |
| No-Antibiotic | A8 | 0.0427 | −0.0030 |
| No-Antibiotic | B8 | 0.0419 | −0.0038 |
| Gentamicin-4 | E7 | 0.0615 | 0.0158 |
| Gentamicin-16 | F7 | 0.0426 | −0.0031 |
| Levo-1 | D2 | 0.1180 | 0.0723 |
| Levo-2 | E2 | 0.0436 | −0.0021 |
| Levo-4 | F2 | 0.0431 | −0.0026 |
| Levo-8 | G2 | 0.0443 | −0.0014 |
| Mero-1 | F1 | 0.2198 | 0.1741 |
| Mero-2 | G1 | 0.1928 | 0.1471 |
| Mero-4 | H1 | 0.1556 | 0.1099 |
| Mero-8 | A2 | 0.0496 | 0.0039 |
| Nitro-32 | B1 | 0.0552 | 0.0095 |
| Nitro-128 | C1 | 0.0539 | 0.0082 |
| Pip/Tazo-16,4 | A4 | 0.0421 | −0.0036 |
| Pip/Tazo-128,4 | B4 | 0.0419 | −0.0038 |
| Tetra-2 | F4 | 0.2084 | 0.1627 |
| Tetra-4 | G4 | 0.2224 | 0.1767 |
| Tetra-8 | H4 | 0.1596 | 0.1139 |
| Tetra-16 | A5 | 0.0539 | 0.0082 |
| TMP/SMX-2,38 | E5 | 0.1209 | 0.0752 |
| TMP/SMX-4,76 | F5 | 0.1016 | 0.0559 |
| Vanco-1 | D3 | 0.0504 | 0.0047 |
| Vanco-2 | E3 | 0.0435 | −0.0022 |
| Vanco-4 | F3 | 0.0425 | −0.0032 |
| Vanco-16 | G3 | 0.0431 | −0.0026 |
| Vanco-32 | H3 | 0.0426 | −0.0031 |

To determine whether bacterial organisms present in the patient samples were resistant or sensitive to a particular antibiotic at a certain concentration, blanked OD readings were compared to a threshold $OD_{600}$ of 0.065 (Table 15). An OD measurement greater than or equal to this threshold was designated Resistant (R) meaning bacterial organisms present in patient sample were resistant to that particular antibiotic at that certain concentration. Any OD measurement less than this threshold was designated Sensitive (S) meaning bacterial organisms present in patient sample were sensitive to that particular antibiotic at that certain concentration.

TABLE 15

| Antibiotic | Well | Mean | Blanked | Result |
| --- | --- | --- | --- | --- |
| Na Azide | E8 | 0.0457 | 0 | S |
| No-Antibiotic | A1 | 0.2217 | 0.1760 | R |
| No-Antibiotic | F8 | 0.2604 | 0.2147 | R |
| No-Antibiotic | G8 | 0.2354 | 0.1897 | R |
| No-Antibiotic | H8 | 0.2446 | 0.1989 | R |
| Amox/Clav-8,4 | G7 | 0.0418 | −0.0039 | S |
| Amox/Clav-32,16 | H7 | 0.0437 | −0.0020 | S |
| Amp-8 | B5 | 0.0417 | −0.0040 | S |
| Amp-16 | C5 | 0.0419 | −0.0038 | S |
| Amp-32 | D5 | 0.0418 | −0.0039 | S |
| Amp/Sulb-8,4 | B2 | 0.0413 | −0.0044 | S |

TABLE 15-continued

| Antibiotic | Well | Mean | Blanked | Result |
|---|---|---|---|---|
| Amp/Sulb-32,16 | C2 | 0.0414 | −0.0043 | S |
| Cefaclor-8 | C8 | 0.2332 | 0.1875 | R |
| Cefaclor-32 | D8 | 0.0600 | 0.0143 | S |
| Cefazolin-2 | G5 | 0.2339 | 0.1882 | R |
| Cefazolin-8 | H5 | 0.2090 | 0.1633 | R |
| Cefazolin-16 | A6 | 0.1468 | 0.1011 | R |
| Cefazolin-32 | B6 | 0.0570 | 0.0113 | S |
| Cefepime-1 | C6 | 0.2416 | 0.1959 | R |
| Cefepime-2 | D6 | 0.2427 | 0.1970 | R |
| Cefepime-4 | E6 | 0.2417 | 0.1960 | R |
| Cefepime-8 | F6 | 0.2404 | 0.1947 | R |
| Cefepime-16 | G6 | 0.2323 | 0.1866 | R |
| Cefepime-32 | H6 | 0.2281 | 0.1824 | R |
| Cefoxitin-4 | C4 | 0.2202 | 0.1745 | R |
| Cefoxitin-8 | D4 | 0.2288 | 0.1831 | R |
| Cefoxitin-32 | E4 | 0.2348 | 0.1891 | R |
| Ceftazidime-4 | A7 | 0.2457 | 0.2000 | R |
| Ceftazidime-8 | B7 | 0.2607 | 0.2150 | R |
| Ceftazidime-16 | C7 | 0.2473 | 0.2016 | R |
| Ceftazidime-32 | D7 | 0.2437 | 0.1980 | R |
| Ceftriaxone-1 | H2 | 0.2485 | 0.2028 | R |
| Ceftriaxone-4 | A3 | 0.2357 | 0.1900 | R |
| Ceftriaxone-8 | B3 | 0.2449 | 0.1992 | R |
| Ceftriaxone-64 | C3 | 0.2356 | 0.1899 | R |
| Cipro-1 | D1 | 0.0441 | −0.0016 | S |
| Cipro-4 | E1 | 0.0423 | −0.0034 | S |
| No-Antibiotic | A8 | 0.0427 | −0.0030 | S |
| No-Antibiotic | B8 | 0.0419 | −0.0038 | S |
| Gentamicin-4 | E7 | 0.0615 | 0.0158 | S |
| Gentamicin-16 | F7 | 0.0426 | −0.0031 | S |
| Levo-1 | D2 | 0.1180 | 0.0723 | R |
| Levo-2 | E2 | 0.0436 | −0.0021 | S |
| Levo-4 | F2 | 0.0431 | −0.0026 | S |
| Levo-8 | G2 | 0.0443 | −0.0014 | S |
| Mero-1 | F1 | 0.2198 | 0.1741 | R |
| Mero-2 | G1 | 0.1928 | 0.1471 | R |
| Mero-4 | H1 | 0.1556 | 0.1099 | R |
| Mero-8 | A2 | 0.0496 | 0.0039 | S |
| Nitro-32 | B1 | 0.0552 | 0.0095 | S |
| Nitro-128 | C1 | 0.0539 | 0.0082 | S |
| Pip/Tazo-16,4 | A4 | 0.0421 | −0.0036 | S |
| Pip/Tazo-128,4 | B4 | 0.0419 | −0.0038 | S |
| Tetra-2 | F4 | 0.2084 | 0.1627 | R |
| Tetra-4 | G4 | 0.2224 | 0.1767 | R |
| Tetra-8 | H4 | 0.1596 | 0.1139 | R |
| Tetra-16 | A5 | 0.0539 | 0.0082 | S |
| TMP/SMX-2,38 | E5 | 0.1209 | 0.0752 | R |
| TMP/SMX-4,76 | F5 | 0.1016 | 0.0559 | S |
| Vanco-1 | D3 | 0.0504 | 0.0047 | S |
| Vanco-2 | E3 | 0.0435 | −0.0022 | S |
| Vanco-4 | F3 | 0.0425 | −0.0032 | S |
| Vanco-16 | G3 | 0.0431 | −0.0026 | S |
| Vanco-32 | H3 | 0.0426 | −0.0031 | S |

In this example, the sample contains bacteria sensitive to amoxicillin/clavulanate, ampicillin, ampicillin/sulbactam, ciprofloxacin, gentamicin, levofloxacin, nitrofurantoin, piperacillin/tazobactam, and vancomycin.

The MIC for each drug can then be provided. The minimum inhibitory concentration (MIC) is the minimum test antibiotic concentration to which the sample is sensitive. An exemplary MIC determination for meropenem based on the results above is depicted in Table 16.

TABLE 16

| Mero [1] | Mero [2] | Mero [4] | Mero [8] | MIC | Interpretation |
|---|---|---|---|---|---|
| S | S | S | S | <=1 | S |
| R | S | S | S | <=2 | I |
| R | R | S | S | <=4 | I |
| R | R | R | S | <=8 | I |
| R | R | R | R | >=8 | R |

Example 4. Validation of ABR Assay Utilizing Liquid Growth Medium

Accuracy

Accuracy was assessed by comparing the antibiotic resistance results of the test method to a consensus of results obtained by standard reference methods. A total of 15 isolated organisms, and 20 routinely processed patient urine samples were tested for resistance to 18 antibiotics, each tested at multiple concentrations for a total of 57 antibiotic concentrations. Accuracy was assessed regarding Specificity (True Negatives), Sensitivity (True Positives), and overall Accuracy (all samples). The assay showed good accuracy in all three categories (Table 17).

TABLE 17

|  | % Accuracy |
|---|---|
| Overall Accuracy | 96% |
| Specificity | 95% |
| Sensitivity | 97% |

Precision

Inter-Assay precision was evaluated by testing five samples over three different days. Intra-Assay precision was evaluated by testing the same five samples in triplicate in a single day. Percent concordance was calculated to measure the precision of results obtained by this assay. The assay demonstrated very good precision (Table 18).

TABLE 18

| | Precision | |
|---|---|---|
| Description | Intra-Assay | Inter-Assay |
| Total # of Matches | 841 | 1388 |
| Total # of Measurements | 855 | 1425 |
| % Concordance | 98% | 97% |

Analytic Sensitivity

Analytic sensitivity was evaluated by creating a dilution series of E. coli and E. faecalis with the lowest bacterial concentration at less than 100 cells/mL for each organism. Each dilution level for each isolate was tested to show reproducibility of results down to the lowest concentration. 98% correlation was observed across all dilution levels for both isolates, indicating the limit of detection (LOD) of this assay is less than 100 cells/ml.

Analytic Specificity

Analytic specificity was evaluated in the context of inhibitory effect of overloading the assay with too many bacterial cells. Lower accuracy (due to false-resistant results) was observed for samples inoculated at high bacterial concentration. This indicates that all samples must be diluted to the specified cell density post pre-culture and before ABR inoculation.

Pre-Culture Duration Determination

This assay utilizes a pre-culture step prior to introducing samples to antibiotics. The duration of this pre-culture incubation was tested at 6 and 16 hours for 2 isolates (E. coli and E. faecalis). Good accuracy for each isolate was observed after both 6 and 16 hour pre-culture incubations, indicating a pre-culture window of 6 to 16 hours for this assay. Results displayed below in Table 19.

TABLE 19

| Description | # Results | Accuracy |
| --- | --- | --- |
| Total # of Matches | 81 | 98% |
| Total # of Measurements | 83 | |

Incubation Duration Determination

Once samples are introduced to antibiotics, they are incubated for 12 to 16 hours. This incubation length was determined by obtaining OD measurements for Precision samples after 12 and 16 hours of incubation. Good percent concordance was observed for all samples across within a 12 to 16 hour incubation window (Table 20).

TABLE 20

| Description | # Targets | % Concordance |
| --- | --- | --- |
| Total # of Matches | 2758 | 97% |
| Total # of Measurements | 2850 | |

Bacterial Growth Confirmation

To confirm turbidity (high OD measurements) are due to bacterial growth, DNA was extracted from wells corresponding to Sensitive and Resistant results and tested for pathogen identification by PCR. Identification results confirm Resistant (turbid) wells contained significantly higher bacterial concentration than Sensitive (clear) wells (Table 21).

TABLE 21

| | Overall (Cells/mL) |
| --- | --- |
| Resistant | 5,170,897,798 |
| Sensitive | 1,341,116 |
| Fold-Diff | 3,856 |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for simultaneously determining the antibiotic susceptibilities of a mixed population of bacteria in a sample from a subject suspected of having an infection, the method comprising:
   (a) applying portions of the sample simultaneously to a plurality of antibiotic-containing growth media, wherein, in a first subset of the antibiotic-containing growth media, each antibiotic-containing growth medium contains a combination of antibiotics and, in a second subset of the antibiotic-containing growth media, each antibiotic-containing growth medium contains one antibiotic, and wherein the bacteria are not isolated from the sample prior to applying to the antibiotic-containing growth media;
   (b) culturing the sample portions on or in the antibiotic-containing growth media for a period of time;
   (c) suspending the bacteria present in each antibiotic-containing medium with a solution and recovering the suspensions;
   (d) measuring an $OD_{600}$ of each suspension, and calculating an adjusted $OD_{600}$ for each suspension, wherein the adjusted $OD_{600}$ of each suspension indicates the susceptibility or resistance of the bacteria from the sample to each combination of antibiotics and to each antibiotic tested alone; and
   (e) providing the susceptibility information to a medical professional to determine antibiotic therapy for the subject.

2. The method according to claim 1, wherein the plurality of antibiotic-containing growth media are in a multi-well assay plate.

3. The method according to claim 2, wherein the antibiotic-containing growth media comprises agar.

4. The method according to claim 3, wherein each of the plurality of wells contains a single antibiotic or a combination of antibiotics.

5. The method according to claim 4, wherein the combination of antibiotics comprises at least two antibiotics, at least three antibiotics, at least four antibiotics, at least five antibiotics, at least six antibiotics, at least seven antibiotics, at least eight antibiotics, at least nine antibiotics, or at least ten antibiotics.

6. The method according to claim 2, wherein different wells of the multi-well plate contain different concentrations of at least one antibiotic in the combination, or of the antibiotic when only one is present.

7. The method according to claim 1, wherein the $OD_{600}$ of the suspension is measured a plurality of times.

8. The method according to claim 1, wherein the adjusted $OD_{600}$ comprises the mean $OD_{600}$ of a plurality of measurements less a background control.

9. The method according to claim 1, wherein the bacteria in the sample are susceptible to an antibiotic, or combination of antibiotics, if the adjusted $OD_{600}$ is less than 0.025.

10. The method according to claim 1, wherein the bacteria in the sample are resistant to an antibiotic, or combination of antibiotics, if the adjusted $OD_{600}$ is greater than or equal to 0.025.

11. The method according to claim 1, wherein the sample is a biological fluid or a biopsy sample.

12. The method according to claim 11, wherein the sample comprises urine, blood, saliva, sputum, pulmonary lavage, vaginal secretions, biopsy tissue, or cerebrospinal fluid.

13. A method for simultaneously determining the antibiotic susceptibilities of a mixed population of bacteria in a sample, the method comprising:
   (a) mixing a quantity of a sample with a growth medium and incubating for a period of time, wherein the sample is from a subject suspected of having an infection;
   (b) applying portions of the incubated sample simultaneously to a plurality of antibiotic-containing growth media, wherein, in a first subset of the antibiotic-containing growth media, each antibiotic-containing growth medium contains a combination of antibiotics and; in a second subset of the antibiotic-containing growth media, each antibiotic-containing growth medium contains one antibiotic; wherein the bacteria are not isolated from the sample prior to applying to the antibiotic-containing growth media;
   (c) culturing the sample portions in the antibiotic-containing growth media for a period of time;
   (d) measuring bacterial growth in the antibiotic-containing growth media by measuring the $OD_{600}$, and calculating an adjusted $OD_{600}$ for each antibiotic-containing growth medium, wherein the adjusted $OD_{600}$ measurements of the antibiotic-containing growth media indicate the susceptibility or resistance of the bacteria, from the sample to each combination of antibiotics and to each antibiotic tested alone; and
   (e) providing the susceptibility information to a medical professional to determine antibiotic therapy for the subject.

14. The method according to claim 13, wherein the plurality of antibiotic-containing growth media are in a multi-well assay plate.

15. The method according to claim 13, wherein the antibiotic-containing media are liquid broth media.

16. The method according to claim 14, wherein each of the plurality of wells contains a single antibiotic or a combination of antibiotics.

17. The method according to claim 14, wherein the combination of antibiotics comprises at least two antibiotics, at least three antibiotics, at least four antibiotics, at least five antibiotics, at least six antibiotics, at least seven antibiotics, at least eight antibiotics, at least nine antibiotics, or at least ten antibiotics.

18. The method according to claim 14, wherein different wells of the multi-well plate contain different concentrations of at least one antibiotic in the combination, or of the antibiotic when only one is present.

19. The method according to claim 18, wherein the $OD_{600}$ of each well is measured one time.

20. The method according to claim 18, wherein the $OD_{600}$ of each sample is measured a plurality of times.

21. The method according to claim 13, wherein the adjusted $OD_{600}$ comprises a single $OD_{600}$ measurement, or a mean $OD_{600}$ of a plurality of measurements, less a background control.

22. The method according to claim 13, wherein the bacteria in the sample are susceptible to an antibiotic, or combination of antibiotics, if the adjusted $OD_{600}$ is less than 0.065.

23. The method according to claim 13, wherein the bacteria in the sample are resistant to an antibiotic, or combination of antibiotics, if the adjusted $OD_{600}$ is greater than or equal to 0.065.

24. The method according to claim 13, wherein the sample is a biological fluid or a biopsy sample.

25. The method according to claim 24, wherein the sample comprises urine, blood, saliva, sputum, pulmonary lavage, vaginal secretions, biopsy tissue, or cerebrospinal fluid.

* * * * *